(12) United States Patent
Yoon et al.

(10) Patent No.: US 11,529,406 B2
(45) Date of Patent: Dec. 20, 2022

(54) CLOSTRIDIUM PERFRINGENS BACTERIOPHAGE CLO-PEP-2 AND USE FOR INHIBITING CLOSTRIDIUM PERFRINGENS PROLIFERATION OF SAME

(71) Applicant: Intron Biotechnology, Inc., Gyeonggi-do (KR)

(72) Inventors: Seong Jun Yoon, Seoul (KR); Soo Youn Jun, Seoul (KR); Hyoun Rok Paik, Incheon (KR); Jee Soo Son, Seoul (KR); Hee Jeong Shin, Gyeonggi-do (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 606 days.

(21) Appl. No.: 16/487,511

(22) PCT Filed: Jan. 11, 2018

(86) PCT No.: PCT/KR2018/000513
§ 371 (c)(1),
(2) Date: Aug. 21, 2019

(87) PCT Pub. No.: WO2018/155814
PCT Pub. Date: Aug. 30, 2018

(65) Prior Publication Data
US 2020/0054042 A1    Feb. 20, 2020

(30) Foreign Application Priority Data
Feb. 24, 2017    (KR) .................. 10-2017-0024557

(51) Int. Cl.
*A61K 35/76*    (2015.01)
*C12N 7/00*    (2006.01)
*A61K 39/08*    (2006.01)

(52) U.S. Cl.
CPC .............. *A61K 39/08* (2013.01); *A61K 35/76* (2013.01); *C12N 7/00* (2013.01)

(58) Field of Classification Search
None
See application file for complete search history.

(56) References Cited

FOREIGN PATENT DOCUMENTS

| KR | 20120076710 A | 7/2012 |
| KR | 101381798 B1 | 4/2014 |
| KR | 20160013243 A | 2/2016 |
| KR | 20160080175 A | 7/2016 |
| WO | WO-2018/155814 A1 | 8/2018 |

OTHER PUBLICATIONS

PCT, PCT/KR2018/000513 (WO 2018/155814), Jan. 11, 2018 (Aug. 30, 2018), Intron Biotechnology, Inc.
Oakley, et al., "Comparative genomics of four closely related Clostridium perfringens bacteriophages reveals variable evolution among core genes with therapeutic potential", BMC Genomics 2011, 12:282.
International Search Report and Written Opinion dated Apr. 24, 2018 by the International Searching Authority for International Application No. PCT/KR2018/000513, filed on Jan. 11, 2018 and published as WO 2018/155814 on Aug. 30, 2018 (Applicant— Intron Biotechnology, Inc.) (Original—8 Pages / Translation—2 pages).

*Primary Examiner* — Sarvamangala Devi
(74) *Attorney, Agent, or Firm* — Ballard Spahr LLP

(57) ABSTRACT

The present invention relates to Siphoviridae bacteriophage Clo-PEP-2 (accession number KCTC 13185BP), separated from nature, which is capable of killing *Clostridium perfringens* and has a genome expressed by sequence number 1 and a method for preventing or treating diseases, induced by *Clostridium perfringens*, by means of a composition comprising the Siphoviridae bacteriophage Clo-PEP-2 as an active ingredient.

1 Claim, 2 Drawing Sheets
Specification includes a Sequence Listing.

[FIG. 1]
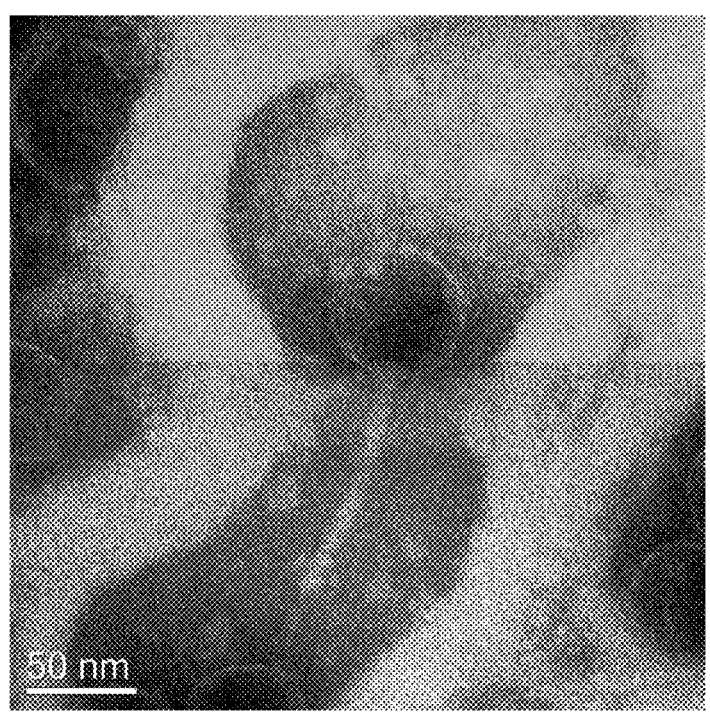

[FIG. 2]
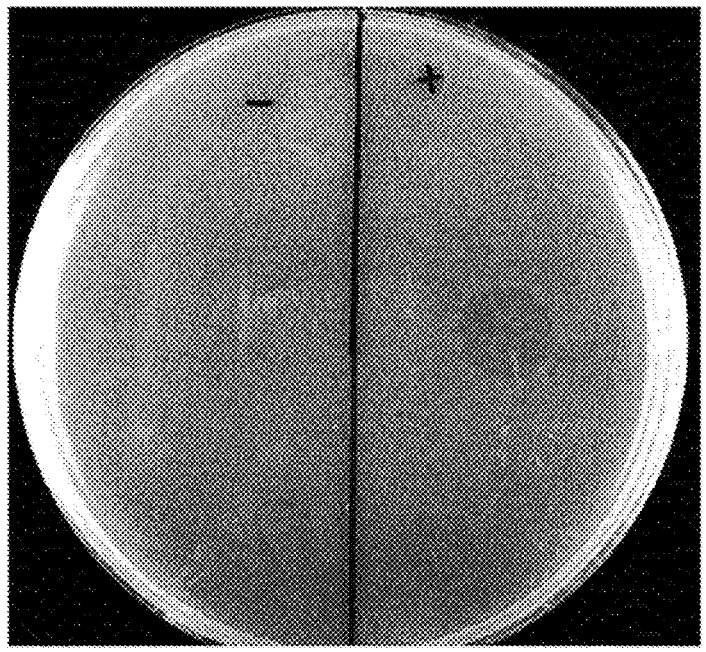

CLOSTRIDIUM PERFRINGENS BACTERIOPHAGE CLO-PEP-2 AND USE FOR INHIBITING CLOSTRIDIUM PERFRINGENS PROLIFERATION OF SAME

CROSS-REFERENCE TO RELATED APPLICATIONS

This application is a U.S. National Phase Application of International Application No. PCT/KR2018/000513, filed Jan. 11, 2018, which claims priority to Korean Application No. 10-2017-0024557, filed Feb. 24, 2017, each of which are hereby incorporated by reference in their entirety.

The Sequence Listing submitted Aug. 21, 2019, as a text file named "08162_0061U1_Sequence_Listing.txt," created on Jul. 26, 2019, and having a size of 50,481 bytes is hereby incorporated by reference pursuant to 37 C.F.R. § 1.52(e)(5).

TECHNICAL FIELD

The present invention relates to a bacteriophage isolated from nature, which infects *Clostridium perfringens* to thus kill *Clostridium perfringens*, and a method of preventing or treating a disease caused by *Clostridium perfringens* using a composition containing the above bacteriophage as an active ingredient. More particularly, the present invention relates to a Siphoviridae bacteriophage Clo-PEP-2 (Accession number: KCTC 13185BP) isolated from nature, which has the ability to kill *Clostridium perfringens* and has the genome represented by SEQ ID NO: 1, and a method of preventing or treating a disease caused by *Clostridium perfringens* using a composition containing the above bacteriophage as an active ingredient.

BACKGROUND ART

*Clostridium perfringens*, which is an aerophobic anaerobe (a bacterium that grows with difficulty or not at all in the presence of oxygen), is a cause of serious diseases in humans or animals such as cattle, pigs, goats and the like, and in particular is a major cause of necrotizing enterocolitis and food poisoning. The main exotoxins produced by *Clostridium perfringens* are present in four forms, namely α, β, ε and i. Depending on the presence or absence of these toxins, *Clostridium perfringens* bacteria are classified into six types from A to F. Among these, *Clostridium perfringens* type A is a typical cause of food poisoning and secretes only α-toxin, and *Clostridium perfringens* type C, which is known to cause necrotizing enteritis, secretes α-toxin and β-toxin.

Recently, the incidence of *Clostridium perfringens* infection has been increasing in the poultry industry, and thus has caused serious damage to farms. In particular, the damage caused by *Clostridium perfringens* infection in broiler chickens is very serious. Recently, the incidence of infections caused by *Clostridium perfringens* has also been increasing in the pig industry, and damage attributable thereto has been increasing. Therefore, it is urgent to establish methods to effectively cope with *Clostridium perfringens* infections.

Although various antibiotics have been used for the prevention or treatment of diseases caused by *Clostridium perfringens*, the incidence of bacteria resistant to these antibiotics is increasing these days, and thus the development of other methods besides antibiotics is urgent.

Recently, the use of bacteriophages as a countermeasure against infectious bacterial diseases has attracted considerable attention. In particular, these bacteriophages are receiving great attention due to strong antibacterial activity against antibiotic-resistant bacteria. Bacteriophages are very small microorganisms infecting bacteria, and are usually simply called "phages". Once a bacteriophage infects a bacterium, the bacteriophage is proliferated inside the bacterial cell. After proliferation, the progeny of the bacteriophage destroy the bacterial cell wall and escape from the host bacteria, demonstrating that the bacteriophage has the ability to kill bacteria. The manner in which the bacteriophage infects bacteria is characterized by very high specificity thereof, and thus the range of types of bacteriophages infecting a specific bacterium is limited. That is, a certain bacteriophage may infect only a specific bacterium, suggesting that a certain bacteriophage is capable of providing an antibacterial effect only for a specific bacterium. Due to this bacterial specificity of bacteriophages, the bacteriophage confers antibacterial effects only upon target bacteria, but does not affect commensal bacteria in the environment or in the intestines of animals. Conventional antibiotics, which have been widely used for bacterial treatment, incidentally influence many other kinds of bacteria. This causes problems such as environmental pollution and the disturbance of normal flora in animals. In contrast, the use of bacteriophages does not disturb normal flora in animals, because the target bacterium is selectively killed. Hence, bacteriophages may be utilized safely, which thus greatly lessens the probability of adverse effects of use thereof compared to antibiotics.

Bacteriophages were first discovered by the English bacteriologist Twort in 1915 when he noticed that *Micrococcus* colonies softened and became transparent due to something unknown. In 1917, the French bacteriologist d'Herelle discovered that *Shigella dysenteriae* in the filtrate of dysentery patient feces was destroyed by something, and further studied this phenomenon. As a result, he independently identified bacteriophages, and named them bacteriophages, which means "eater of bacteria". Since then, bacteriophages acting against such pathogenic bacteria as *Shigella, Salmonella Typhi*, and *Vibrio cholerae* have been continually identified.

Owing to the unique ability of bacteriophages to kill bacteria, bacteriophages have attracted attention as a potentially effective countermeasure against bacterial infection since their discovery, and a lot of research related thereto has been conducted. However, since penicillin was discovered by Fleming, studies on bacteriophages have continued only in some Eastern European countries and the former Soviet Union, because the spread of antibiotics was generalized. Since 2000, the limitations of conventional antibiotics have become apparent due to the increase in antibiotic-resistant bacteria, and the possibility of developing bacteriophages as a substitute for conventional antibiotics has been highlighted, and thus bacteriophages are again attracting attention as antibacterial agents.

As demonstrated above, bacteriophages tend to be highly specific for target bacteria. Because of the high specificity of bacteriophages to bacteria, bacteriophages frequently exhibit an antibacterial effect only for certain strains of bacteria, even within the same species. In addition, the antibacterial strength of bacteriophages may vary depending on the target bacterial strain. Therefore, it is necessary to collect many kinds of bacteriophages that are useful in order to effectively control specific bacteria. Hence, in order to develop an effective bacteriophage utilization method for controlling *Clostridium perfringens*, many kinds of bacteriophages that exhibit antibacterial action against *Clostridium perfringens* must be acquired. Furthermore, the resulting bacteriophages need to be screened as to whether or not they are superior to others in view of the aspects of antibacterial strength and spectrum.

DISCLOSURE

Technical Problem

Therefore, the present inventors endeavored to develop a composition applicable for the prevention or treatment of a disease caused by *Clostridium perfringens* using a bacteriophage that is isolated from nature and is capable of killing *Clostridium perfringens*, and further to establish a method of preventing or treating a disease caused by *Clostridium perfringens* using the composition. As a result, the present inventors isolated a bacteriophage suitable for this purpose from nature and determined the sequence of the genome, which distinguishes the isolated bacteriophage from other bacteriophages. Then, the present inventors developed a composition containing the bacteriophage as an active ingredient, and ascertained that this composition is capable of being used to effectively prevent or treat a disease caused by *Clostridium perfringens*, thus culminating in the present invention.

Accordingly, it is an object of the present invention to provide a Siphoviridae bacteriophage Clo-PEP-2 (Accession number: KCTC 13185BP) isolated from nature, which has the ability to specifically kill *Clostridium perfringens* and has the genome represented by SEQ ID NO: 1.

It is another object of the present invention to provide a composition applicable for preventing or treating a disease caused by *Clostridium perfringens*, which contains, as an active ingredient, an isolated bacteriophage Clo-PEP-2 (Accession number: KCTC 13185BP) infecting *Clostridium perfringens* to thus kill *Clostridium perfringens*.

It is another object of the present invention to provide a method of preventing or treating a disease caused by *Clostridium perfringens* using the composition applicable for preventing or treating a disease caused by *Clostridium perfringens*, which contains, as an active ingredient, the isolated bacteriophage Clo-PEP-2 (Accession number: KCTC 13185BP) infecting *Clostridium perfringens* to thus kill *Clostridium perfringens*.

It is another object of the present invention to provide a disinfectant for preventing or treating a disease caused by *Clostridium perfringens* using the above-described composition.

It is another object of the present invention to provide a drinking-water additive for preventing or treating a disease caused by *Clostridium perfringens* using the above-described composition.

It is another object of the present invention to provide a feed additive effective upon feeding by preventing or treating a disease caused by *Clostridium perfringens* using the above-described composition.

Technical Solution

The present invention provides a Siphoviridae bacteriophage Clo-PEP-2 (Accession number: KCTC 13185BP) isolated from nature, which has the ability to specifically kill *Clostridium perfringens* and has the genome represented by SEQ ID NO: 1, and a method of preventing or treating a disease caused by *Clostridium perfringens* using a composition containing the Siphoviridae bacteriophage Clo-PEP-2 as an active ingredient.

The bacteriophage Clo-PEP-2 was isolated by the present inventors and then deposited at Korean Collection for Type Cultures, Korea Research Institute of Bioscience and Biotechnology on Jan. 11, 2017 (Accession number: KCTC 13185BP).

The present invention also provides a disinfectant, a drinking-water additive, and a feed additive applicable for the prevention or treatment of a disease caused by *Clostridium perfringens*, which contain the bacteriophage Clo-PEP-2 as an active ingredient.

Since the bacteriophage Clo-PEP-2 contained in the composition of the present invention kills *Clostridium perfringens* effectively, it is effective in the prevention (prevention of infection) or treatment (treatment of infection) of a disease caused by *Clostridium perfringens*. Therefore, the composition of the present invention is capable of being utilized for the prevention and treatment of a disease caused by *Clostridium perfringens*.

As used herein, the terms "prevention" and "prevent" refer to (i) prevention of a *Clostridium perfringens* infection and (ii) inhibition of the development of a disease caused by a *Clostridium perfringens* infection.

As used herein, the terms "treatment" and "treat" refer to all actions that (i) suppress a disease caused by *Clostridium perfringens* and (ii) alleviate the pathological condition of the disease caused by *Clostridium perfringens*.

As used herein, the terms "isolate", "isolating", and "isolated" refer to actions that isolate bacteriophages from nature by using diverse experimental techniques and that secure characteristics that can distinguish the bacteriophage of the present invention from others, and further include the action of proliferating the bacteriophage of the present invention using bioengineering techniques so that the bacteriophage is industrially applicable.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspension agents, and preservatives, in addition to the above ingredients.

The bacteriophage Clo-PEP-2 is contained as an active ingredient in the composition of the present invention. The bacteriophage Clo-PEP-2 is contained at a concentration of $1 \times 10^1$ pfu/ml to $1 \times 10^{30}$ pfu/ml or $1 \times 10^1$ pfu/g to $1 \times 10^{30}$ pfu/g, and preferably at a concentration of $1 \times 10^4$ pfu/ml to $1 \times 10^{15}$ pfu/ml or $1 \times 10^4$ pfu/g to $1 \times 10^{15}$ pfu/g.

The composition of the present invention may be formulated using a pharmaceutically acceptable carrier and/or excipient in accordance with a method that may be easily carried out by those skilled in the art to which the present invention belongs, in order to prepare the same in a unit dosage form or insert the same into a multi-dose container. Here, the formulation thereof may be provided in the form of a solution, a suspension, or an emulsion in an oil or aqueous medium, or in the form of an extract, a powder, a granule, a tablet, or a capsule, and may additionally contain a dispersant or a stabilizer.

The composition of the present invention may be prepared as a disinfectant, a drinking-water additive, or a feed additive depending on the purpose of use thereof, without limitation thereto. In order to improve the effectiveness thereof, bacteriophages that confer antibacterial activity against other bacterial species may be further included in the composition of the present invention. In addition, other kinds of bacteriophages that have antibacterial activity against Clostridium perfringens may be further included in the composition of the present invention. These bacteriophages may be combined appropriately so as to maximize the antibacterial effects thereof, because their antibacterial activities against Clostridium perfringens may vary from the aspects of antibacterial strength and spectrum.

Advantageous Effects

According to the present invention, the method of preventing or treating a disease caused by Clostridium perfringens using the composition containing the bacteriophage Clo-PEP-2 as an active ingredient can have the advantage of very high specificity for Clostridium perfringens, compared to conventional methods based on existing antibiotics. This means that the composition can be used for preventing or treating a disease caused by Clostridium perfringens without affecting other bacteria, namely useful commensal bacteria, and has fewer side effects attributable to the use thereof. Typically, when antibiotics are used, commensal bacteria are also damaged, ultimately lowering the immunity of animals and thus entailing various side effects owing to the use thereof. Meanwhile, in the case of various bacteriophages exhibiting antibacterial activity against the same species of bacteria, the antibacterial activities of the bacteriophages are different with regard to antibacterial strength and spectrum [the spectrum of the antibacterial activity of the bacteriophages applied to individual bacteria strains in terms of the strains of various bacteria belonging to Clostridium perfringens, bacteriophages usually being effective only on some bacterial strains, even within the same species, and the antibacterial activity of bacteriophages thus depending on the bacterial strain even for the same species of bacteria]. Accordingly, the present invention can provide antibacterial activity against Clostridium perfringens discriminating from that of other bacteriophages acting on Clostridium perfringens. This provides a great variety of effects in applicability to industrial fields.

DESCRIPTION OF DRAWINGS

FIG. 1 is an electron micrograph showing the morphology of the bacteriophage Clo-PEP-2.

FIG. 2 is a photograph showing the results of an experiment on the ability of the bacteriophage Clo-PEP-2 to kill Clostridium perfringens, in which the clear zone is a plaque formed by lysis of the bacteria.

MODE FOR INVENTION

Hereinafter, the present invention will be described in more detail with reference to Examples. However, the Examples are merely examples of the present invention, and the scope of the present invention is not limited to the Examples.

Example 1

Isolation of Bacteriophage Capable of Killing Clostridium Perfringens

Samples were collected from nature to isolate the bacteriophage capable of killing Clostridium perfringens. Here, the Clostridium perfringens strains used for the bacteriophage isolation had been previously isolated and identified as Clostridium perfringens by the present inventors.

The procedure for isolating the bacteriophage is described in detail hereinafter. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with Clostridium perfringens at a ratio of 1/1000, and then cultured at 37° C. for 3 to 4 hr under anaerobic conditions. After completion of the culture, centrifugation was performed at 8,000 rpm for 20 min and a supernatant was recovered. The recovered supernatant was inoculated with Clostridium perfringens at a ratio of 1/1000, and then cultured at 37° C. for 3 to 4 hr under anaerobic conditions. When the sample contained the bacteriophage, the above procedure was repeated a total of 5 times in order to sufficiently increase the number (titer) of bacteriophages. After repeating the procedure 5 times, the culture broth was subjected to centrifugation at 8,000 rpm for 20 min. After centrifugation, the recovered supernatant was filtered using a 0.45 μm filter. The obtained filtrate was used in a typical spot assay for examining whether or not a bacteriophage capable of killing Clostridium perfringens was included therein.

The spot assay was performed as follows: TSB culture medium was inoculated with Clostridium perfringens at a ratio of 1/1000, and then cultured at 37° C. overnight under anaerobic conditions. 3 ml ($OD_{600}$ of 1.5) of the culture broth of Clostridium perfringens prepared above was spread on a TSA (Tryptic Soy Agar: casein digest, 15 g/L; soybean digest, 5 g/L; NaCl, 5 g/L; agar, 15 g/L) plate in an anaerobic incubator. The spread plate culture medium was left in the anaerobic incubator for about 30 min to thus dry the spread solution. After drying, 10 μl of the prepared filtrate was spotted onto the plate culture medium on which Clostridium perfringens was spread and then left to dry for about 30 min in the anaerobic incubator. After drying, the plate culture medium that was subjected to spotting was cultured without shaking at 37° C. for one day under anaerobic conditions, and then examined for the formation of clear zones at the positions where the filtrate was dropped. In the case in which the filtrate generated a clear zone, it was judged that the bacteriophage capable of killing Clostridium perfringens was included therein. Through the above examination, it was possible to obtain a filtrate containing the bacteriophage having the ability to kill Clostridium perfringens.

The pure bacteriophage was isolated from the filtrate confirmed above to have the bacteriophage capable of killing Clostridium perfringens. A conventional plaque assay was used to isolate the pure bacteriophage. In detail, a plaque formed in the course of the plaque assay was recovered using a sterilized tip, which was then added to the culture broth of Clostridium perfringens, followed by culturing at 37° C. for 4 to 5 hr under anaerobic conditions. After the culturing, centrifugation was performed at 8,000 rpm for 20 min to obtain a supernatant. The Clostridium perfringens culture broth was added to the obtained supernatant at a volume ratio of 1/50, followed by culturing at 37° C. for 4 to 5 hr under anaerobic conditions. In order to increase the number of bacteriophages, the above procedure was repeated at least 5 times. Then, centrifugation was performed at 8,000 rpm for 20 min in order to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, the solution containing the pure bacteriophage was obtained. The procedure for isolating the pure bacteriophage was repeated in its entirety until the generated plaques became similar to each other with respect to size and morphology. In addition, final isolation of the pure bacteriophage was confirmed using electron microscopy. The above procedure was repeated until the isolation of the pure bacteriophage was confirmed using electron microscopy. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics thereof, the novel bacteriophage that was isolated above was confirmed to be a Siphoviridae bacteriophage.

The solution containing the pure bacteriophage confirmed above was subjected to the following purification process. The *Clostridium perfringens* culture broth was added to the solution containing the pure bacteriophage at a volume ratio of 1/50 based on the total volume of the bacteriophage solution, followed by further culturing for 4 to 5 hr under anaerobic conditions. After the culturing, centrifugation was performed at 8,000 rpm for 20 min to obtain a supernatant. This procedure was repeated a total of 5 times in order to obtain a solution containing a sufficient number of bacteriophages. The supernatant obtained from the final centrifugation was filtered using a 0.45 µm filter, followed by a conventional polyethylene glycol (PEG) precipitation process. Specifically, PEG and NaCl were added to 100 ml of the filtrate reaching 10% PEG 8000/0.5 M NaCl, which was then left at 4° C. for 2 to 3 hr. Thereafter, centrifugation was performed at 8,000 rpm for 30 min to obtain the bacteriophage precipitate. The resulting bacteriophage precipitate was suspended in 5 ml of a buffer (10 mM Tris-HCl, 10 mM MgSO$_4$, 0.1% gelatin, pH 8.0). The resulting material may be referred to as a bacteriophage suspension or bacteriophage solution.

As a result, the pure bacteriophage purified above was collected, was named the bacteriophage Clo-PEP-2, and deposited under the Budapest Treaty on the International Procedure at the Korean Collection for Type Cultures, Korea Research Institute of Bioscience and Biotechnology (KRIBB), 125 Gwahak-ro, Yuseong-gu, Daijeon 305-806, Republic of Korea; the deposit was made on Jan. 11, 2017 (Accession number: KCTC 13185BP).

Example 2

Separation and Sequence Analysis of Genome of Bacteriophage Clo-PEP-2

The genome of the bacteriophage Clo-PEP-2 was separated as follows. The genome was separated from the bacteriophage suspension obtained using the same method as in Example 1. First, in order to eliminate DNA and RNA of *Clostridium perfringens* included in the suspension, 200 U of each of DNase I and RNase A was added to 10 ml of the bacteriophage suspension and then left at 37° C. for 30 min. After being left for 30 min, in order to stop the DNase I and RNase A activity, 500 µl of 0.5 M ethylenediaminetetraacetic acid (EDTA) was added thereto, and the resulting mixture was then left for 10 min. In addition, the resulting mixture was further left at 65° C. for 10 min, and 100 µl of proteinase K (20 mg/ml) was then added thereto so as to break the outer wall of the bacteriophage, followed by reacting at 37° C. for 20 min. Thereafter, 500 µl of 10% sodium dodecyl sulfate (SDS) was added thereto, followed by reacting at 65° C. for 1 hr. After reaction for 1 hr, 10 ml of the solution of phenol:chloroform:isoamyl alcohol, mixed at a component ratio of 25:24:1, was added to the reaction solution, followed by mixing thoroughly. In addition, the resulting mixture was subjected to centrifugation at 13,000 rpm for 15 min to thus separate layers. Among the separated layers, the upper layer was selected, and isopropyl alcohol was added thereto at a volume ratio of 1.5, followed by centrifugation at 13,000 rpm for 10 min in order to precipitate the genome. After the precipitate was recovered, 70% ethanol was added to the precipitate, followed by centrifugation at 13,000 rpm for 10 min to wash the precipitate. The washed precipitate was recovered, vacuum-dried and then dissolved in 100 µl of water. This procedure was repeated to thus obtain a large amount of the genome of the bacteriophage Clo-PEP-2.

Information on the sequence of the genome of the bacteriophage Clo-PEP-2 obtained above was secured by performing next-generation sequencing analysis using an Illumina Mi-Seq apparatus provided by the National Instrumentation Center for Environmental Management, Seoul National University. The finally analyzed genome of the bacteriophage Clo-PEP-2 had a size of 39,456 bp, and the whole genome sequence is represented by SEQ ID NO: 1.

The homology (similarity) of the bacteriophage Clo-PEP-2 genomic sequence obtained above with previously reported bacteriophage genomic sequences was investigated using BLAST on the web. Based on the results of the BLAST investigation, the genomic sequence of the bacteriophage Clo-PEP-2 was found to have homology with the sequence of the *Clostridium perfringens* bacteriophage phi130 (GenBank Accession number: JF767208.1), but the identity thereof was low, namely about 69%. Also, the bacteriophage Clo-PEP-2 has an annular genome and *Clostridium perfringens* bacteriophage phi130 has a linear genome, and thus there is a significant difference in the genomic shape in addition to the sequence between the genomes of these two bacteriophages. Furthermore, the number of open reading frames (ORFs) on the bacteriophage Clo-PEP-2 genome is 64, whereas the *Clostridium perfringens* bacteriophage phi130 has 55 open reading frames, from which these two bacteriophages are also evaluated to be different.

Therefore, it can be concluded that the bacteriophage Clo-PEP-2 is a novel bacteriophage different from conventionally reported bacteriophages. Moreover, since the antibacterial strength and spectrum of bacteriophages typically depend on the type of bacteriophage, it is considered that the bacteriophage Clo-PEP-2 can provide antibacterial activity different from that of any other bacteriophages reported previously.

Example 3

Investigation of Killing Ability of Bacteriophage Clo-PEP-2 for *Clostridium Perfringens*

The killing ability of the isolated bacteriophage Clo-PEP-2 for *Clostridium perfringens* was investigated. In order to evaluate the killing ability, the formation of clear zones was observed using a spot assay in the same manner as described in connection with Example 1. A total of 10 strains that had been isolated and identified as *Clostridium*

*perfringens* by the present inventors were used as *Clostridium perfringens* for the investigation of killing ability. The bacteriophage Clo-PEP-2 had the ability to kill a total of 9 strains, among 10 strains of *Clostridium perfringens*, that is, the experimental target. The representative experimental results thereof are shown in FIG. 2. Meanwhile, the ability of the bacteriophage Clo-PEP-2 to kill *Bordetella bronchiseptica, Enterococcus faecalis, Enterococcus faecium, Streptococcus mitis, Streptococcus uberis* and *Pseudomonas aeruginosa* was also measured. Consequently, the bacteriophage Clo-PEP-2 was found not to have the ability to kill these microorganisms.

Therefore, it can be concluded that the bacteriophage Clo-PEP-2 has high ability to kill *Clostridium perfringens* and an antibacterial effect against many *Clostridium perfringens* strains, indicating that the bacteriophage Clo-PEP-2 can be used as an active ingredient of the composition for preventing or treating diseases caused by *Clostridium perfringens*.

Example 4

Experiment for Prevention of *Clostridium Perfringens* Infection Using Bacteriophage Clo-PEP-2

100 μl of a bacteriophage Clo-PEP-2 solution at a level of $1\times10^8$ pfu/ml was added to a tube containing 9 ml of a TSB culture medium. To another tube containing 9 ml of a TSB culture medium, only the same amount of TSB culture medium was further added. A *Clostridium perfringens* culture broth was then added to each tube under anaerobic conditions so that absorbance reached about 0.5 at 600 nm. After addition of *Clostridium perfringens*, the tubes were cultured at 37° C. under anaerobic conditions, during which the growth of *Clostridium perfringens* was observed. As shown in Table 1 below, it was observed that the growth of *Clostridium perfringens* was inhibited in the tube to which the bacteriophage Clo-PEP-2 solution was added, whereas the growth of *Clostridium perfringens* was not inhibited in the tube to which the bacteriophage solution was not added.

TABLE 1

Growth inhibition of *Clostridium perfringens*

| Classification | $OD_{600}$ absorbance value | | |
|---|---|---|---|
| | 0 min after culture | 60 min after culture | 120 min after culture |
| Not added with bacteriophage solution | 0.5 | 0.7 | 1.3 |
| Added with bacteriophage solution | 0.5 | 0.3 | 0.2 |

The above results show that the bacteriophage Clo-PEP-2 of the present invention not only inhibits the growth of *Clostridium perfringens* but also has the ability to kill *Clostridium perfringens*. Therefore, it is concluded that the bacteriophage Clo-PEP-2 can be used as an active ingredient of the composition for preventing diseases caused by *Clostridium perfringens*.

Example 5

Animal Testing for Preventing Disease Caused by *Clostridium Perfringens* Using Bacteriophage Clo-PEP-2

The preventive effect of the bacteriophage Clo-PEP-2 on diseases caused by *Clostridium perfringens* was evaluated using weaning pigs. 20 of 25-day-old weaning pigs were divided into a total of 2 groups of 10 pigs per group and reared separately in experimental pig-rearing rooms (1.1 m×1.0 m), and the test was performed for 14 days. The surrounding environment was controlled using a heater, and the temperature and humidity in the pig rooms were maintained constant, and the pig room floors were washed every day. A feed containing $1\times10^8$ pfu/g of bacteriophage Clo-PEP-2 was supplied to pigs in the experimental group (administered with feed containing the bacteriophage) in a typical feeding manner starting from the test until the end of the test. In contrast, a feed having the same composition but excluding bacteriophage Clo-PEP-2 was supplied to pigs in the control group (administered with feed not containing the bacteriophage) in the same feeding manner starting from the test until the end of the test. For 2 days from the seventh day after the start of the test, the feed was further added with $1\times10^8$ pfu/g of *Clostridium perfringens* and then supplied to all of the pigs in the experimental group (administered with feed containing the bacteriophage) and the control group (administered with feed not containing the bacteriophage) twice a day, thereby inducing infection with *Clostridium perfringens*. The detected level of *Clostridium perfringens* in the feces of all test animals was examined daily from the date of the feeding with the feed containing *Clostridium perfringens* (from the seventh day after the start of the test), and the extent of diarrhea of the pigs was also examined.

The detection of *Clostridium perfringens* in feces was carried out as follows. The fecal sample was spread on a *Clostridium-perfringens*-selective medium (a TSC agar plate; OXOID) and then cultured at 37° C. for 18 to 24 hr under anaerobic conditions. Among the resulting colonies, colonies presumed to be *Clostridium perfringens* were isolated. The colonies thus obtained were used as samples and subjected to polymerase chain reaction (PCR) specific to *Clostridium perfringens*, and thus whether or not the corresponding colonies were *Clostridium perfringens* was finally confirmed.

The extent of diarrhea was determined by measuring according to a diarrhea index. The diarrhea index was measured using a commonly used Fecal Consistency (FC) score (normal: 0, soft stool: 1, loose diarrhea: 2, severe diarrhea: 3).

The results are shown in Tables 2 and 3 below.

TABLE 2

Results of detection of Clostridium perfringens (mean)

| Classification | Number of colonies of *Clostridium perfringens* bacteria detected per plate medium dish | | | | | | | |
|---|---|---|---|---|---|---|---|---|
| | D7 | D8 | D9 | D10 | D11 | D12 | D13 | D14 |
| Control group (administered with feed not containing bacteriophage) | 20 | 18 | 15 | 14 | 16 | 15 | 14 | 13 |
| Experimental group (administered with feed containing bacteriophage) | 10 | 7 | 4 | 3 | 1 | 0 | 0 | 0 |

TABLE 3

Diarrhea index

| Classification | D7 | D8 | D9 | D10 | D11 | D12 | D13 | D14 |
|---|---|---|---|---|---|---|---|---|
| Control group (administered with feed not containing bacteriophage) | 1.1 | 1.4 | 2.0 | 1.5 | 1.4 | 1.5 | 1.4 | 1.4 |
| Experimental group (administered with feed containing bacteriophage) | 0.5 | 0.3 | 0.2 | 0 | 0 | 0 | 0 | 0 |

As is apparent from the above results, it can be concluded that the bacteriophage Clo-PEP-2 of the present invention is very effective in the prevention of diseases caused by *Clostridium perfringens*.

Example 6

Treatment of Disease Caused by *Clostridium Perfringens* Using Bacteriophage Clo-PEP-2

The therapeutic effect of the bacteriophage Clo-PEP-2 on diseases caused by *Clostridium perfringens* was evaluated as follows. 2 groups of forty 2-day-old chicks per group were prepared and reared separately, and the test was performed for 14 days. For 3 days from the fifth day after the start of the test, a feed containing $1 \times 10^7$ cfu/g of *Clostridium perfringens* was supplied in a typical feeding manner. From the last day of feeding with feed containing *Clostridium perfringens*, *Clostridium perfringens* was found in the feces of both groups. From the next day (the eighth day after the start of the test) after the feeding with the feed containing *Clostridium perfringens* for 3 days, a feed containing $1 \times 10^8$ pfu/g of bacteriophage Clo-PEP-2 was supplied to chicks in the experimental group (administered with feed containing the bacteriophage) in a typical feeding manner. In contrast, a feed having the same composition but excluding bacteriophage Clo-PEP-2 was supplied to chicks in the control group (administered with feed not containing the bacteriophage) in the same manner. From the ninth day after the start of the test, the number of *Clostridium perfringens* bacteria in the feces of the test animals was measured. A *Clostridium-perfringens*-selective medium (a TSC agar plate) was used to prevent interference with other contaminating bacteria in the measurement of the number of *Clostridium perfringens* bacteria in this example. The sample was spread on the selective medium under anaerobic conditions and then cultured at 37° C. for 18 to 24 hr under anaerobic conditions. Colonies presumed to be *Clostridium perfringens* were isolated from the selective medium, after which *Clostridium perfringens* was identified through polymerase chain reaction (PCR) (the case where the number of colonies identified as *Clostridium perfringens* through PCR is $10^2$ cfu/ml or more=2, the case where the number of colonies identified as *Clostridium perfringens* through PCR is $10^1 \sim 10^2$ cfu/ml=1, and the case where the number of colonies identified as *Clostridium perfringens* through PCR is $10^0 \sim 10^1$ cfu/ml=0). The results are shown in Table 4 below.

TABLE 4

Results of measurement of the number of *Clostridium perfringens* bacteria (mean)

| | Day | | | | | |
|---|---|---|---|---|---|---|
| | D9 | D10 | D11 | D12 | D13 | D14 |
| Control group (administered with feed not containing bacteriophage) | 1.0 | 1.1 | 1.0 | 1.1 | 1.1 | 1.2 |
| Experimental group (administered with feed containing bacteriophage) | 0.2 | 0.1 | 0 | 0 | 0 | 0 |

As is apparent from the above results, it can be concluded that the bacteriophage Clo-PEP-2 of the present invention is very effective in the treatment of diseases caused by *Clostridium perfringens*.

Example 7

Preparation of Feed Additive and Feed

A feed additive was prepared using a bacteriophage Clo-PEP-2 solution so that a bacteriophage Clo-PEP-2 was contained in an amount of $1 \times 10^9$ pfu for 1 g of the feed additive. The method of preparing the feed additive was as follows: Maltodextrin (50%, w/v) was added to the bacteriophage solution, and the resulting mixture was then freeze-dried. Finally, the dried mixture was ground into fine powder. In the above-described preparation procedure, the drying process may be replaced with drying under reduced pressure, drying with heat, or drying at room temperature. In order to prepare the control for comparison, the feed additive that did not contain the bacteriophage but contained a buffer (10 mM Tris-HCl, 10 mM $MgSO_4$, 0.1% gelatin, pH 8.0) used to prepare the bacteriophage solution was prepared.

The two kinds of feed additives thus prepared were each mixed with a poultry-based feed at a weight ratio of 1,000, thus ultimately preparing two kinds of feed.

Example 8

Preparation of Drinking-Water Additive and Disinfectant

A drinking-water additive and a disinfectant were prepared in the same manner because they differ only in utilization and are the same in dosage form. The drinking-water additive (or disinfectant) was prepared using a bacteriophage Clo-PEP-2 solution so that a bacteriophage Clo-PEP-2 was contained in an amount of $1 \times 10^9$ pfu for 1 ml of the drinking-water additive (or disinfectant). In the method of preparing the drinking-water additive (or disinfectant), the bacteriophage Clo-PEP-2 solution was added so that the bacteriophage Clo-PEP-2 was contained in an amount of $1 \times 10^9$ pfu for 1 ml of the buffer used to prepare the bacteriophage solution, and mixing was sufficiently performed. In order to prepare the control for comparison, the buffer used to prepare the bacteriophage solution was used without change as the drinking-water additive (or disinfectant) that did not contain the bacteriophage.

The two prepared kinds of drinking-water additives (or disinfectants) were diluted with water at a volume ratio of 1,000, thus ultimately preparing drinking water or disinfectants.

Example 9

Confirmation of Feeding Effect on Chicken Farming

An improvement in chicken farming as the result of feeding was investigated using the feed, drinking water or disinfectant prepared in Examples 7 and 8. In particular, the investigation was focused on mortality. 120 of 2-day-old chicks were divided into three groups, each including 40 chicks (group A: fed with the feed, group B: fed with the drinking water, and group C: treated with the disinfectant), and the test was performed for four weeks. Each group was divided into subgroups each including 20 chicks, and the subgroups were classified into a subgroup to which the bacteriophage Clo-PEP-2 was applied (subgroup-①) and a subgroup to which the bacteriophage was not applied (subgroup-②). In the present test, the chicks were raised separately in individual subgroups. The subgroups were classified and named as shown in Table 5 below.

TABLE 5

Subgroup classification and expression in chicken feeding test

| Application | Bacteriophage Clo-PEP-2 is applied | Bacteriophage is not applied |
|---|---|---|
| Group fed with feed | A-① | A-② |
| Group fed with drinking water | B-① | B-② |
| Group treated with disinfectant | C-① | C-② |

In the case of provision of the feed, the feed prepared in Example 7 was provided according to a typical feeding method as classified in Table 5, and the drinking water prepared in Example 8 was provided according to a typical drinking-water provision method as classified in Table 5. In the case of disinfection, the disinfection was carried out alternately with existing disinfection 3 times a week. Disinfection using a typical disinfectant was not performed on the day on which the disinfectant of the present invention was sprayed. The test results are shown in Table 6 below.

TABLE 6

Mortality in chicken feeding test

| Group | Mortality (%) |
|---|---|
| A-① | 0 |
| A-② | 40 |
| B-① | 5 |
| B-② | 40 |
| C-① | 0 |
| C-② | 40 |

The above results indicate that the provision of the feed and the drinking water prepared according to the present invention and the disinfection according to the present invention were effective in reducing mortality upon chicken farming. Therefore, it is concluded that the composition of the present invention is capable of being effectively applied to improving the results of chicken feeding.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

[Accession Number]
Name of Depositary Authority: KCTC
Accession number: KCTC 13185BP
Accession date: 20170111

---

The invention claimed is:

1. A method of preventing or treating a disease caused by *Clostridium perfringens*, the method comprising:

administering to an animal other than a human a composition comprising an effective amount of Siphoviridae bacteriophage Clo-PEP-2 having a genome set forth in SEQ ID NO: 1 and deposited under the accession number of KCTC 13185BP, which has an ability to kill *Clostridium perfringens*.

* * * * *

SEQUENCE LISTING

<160> NUMBER OF SEQ ID NOS: 1

<210> SEQ ID NO 1
<211> LENGTH: 39456
<212> TYPE: DNA
<213> ORGANISM: bacteriophage Clo-PEP-2

<400> SEQUENCE: 1

| | | | | | | |
|---|---|---|---|---|---|---|
| tatccttctc | gctatctaaa | aataaagttt | caaagattat | attaggcgcg | tttatatttc | 60 |
| tcatttcata | atatttatca | ctatatttaa | cacctctatt | tttaaaccct | aaactagaaa | 120 |
| agttttttgca | cattctttca | gcataaggct | tagctcttga | attgttagca | atccaagctt | 180 |
| cacaaccttg | tccaccacca | atattaccat | gccaagatat | aaataaatcc | aaaatttgtg | 240 |
| catttgcttt | ccttgcacct | tctgacaact | ctccgttttg | agtgttagcg | ttggagcaac | 300 |
| aatcaattat | agtatgtcca | tattgttcca | ttattttttt | gaattcaaaa | tgaagaggtt | 360 |
| tcatagcgtc | cacttcatct | cttaatcctt | tagcccctct | gcaatttca | gaatgaccat | 420 |
| atctacttcc | aattatcaca | ttatcacctt | cctttatcta | tattttacca | ctttaattac | 480 |
| aattattgca | acgatataac | tcccaaaatt | cattaatcgg | cttttatgg | ataatttctt | 540 |
| tctctctttt | ttgtatcgat | ggtgtttcag | tttcttgaga | aggtttttga | actgtagctt | 600 |

```
tttgcataaa attattttct ttattttcat gctcaaaccc ttttcttttc ccttctaatt      660
tatatttaaa tttcatttct ctatcagatt caactataaa ataatccttt tctctaattt      720
caactttata atctccccaa cttaatttat ctatataaat gttataaggt aacattgtgt      780
tgatacactc ttgaattatt tcatctattt caattctaca aatatatttc ccctcaacta      840
actctgttgt ataaatatta tctgtgtctg tttcagttaa taaagagttt atatcctcat      900
ttgcatagaa tggaacatct ccaaacttag tttgttgaat acagttttta tttcctataa      960
cagataaatc accgcctatt ataactttgt tataaaaatt agccacatcc ctatctaatg     1020
taagtaaatg attaccacta ccatcgtttg accaaaatcc aaaattattg gtatataaag     1080
ctactgaacc tctgtcccta ctatctaaat aaccaaacat tctactttct tgattctttt     1140
tatcgaaata catatttaat ccattcatgt taaattcttc ataaaccgtt ataggtgtcg     1200
gttgtgtaag tccttcttta tcaaaacgca tataattgta ataattagaa ccatcacctc     1260
tataagcaat ttgcgcatac gccccttttt cgtttgtcaa tccaacgaca tcatcaccag     1320
taacaacatt tctcaacgct tgtaatgaac cgtttatttg atttttctctt aaaaaagaat    1380 atacatgcac accattgtta tttaatctta ctgacaattt acctctgtta agttgagaaa     1440
atccgttttc atctaaaatt gtactcgcaa cacttatagc tccaccttct gtaagacctt     1500
tgtttacact atttataatt gaatcaggtg ttaatttttg aaaaacttcg ctataacttg     1560
cttctttaga tatataaggt aattcctttt cacctttat aatcataatt tcagtaaaac      1620
caagtgagtt tgaattatct ccaccatatt caaatgttat atatgcactt tttgcattag     1680
gtggcacata aatttatt gttactttt taaaggattc atcttctgaa tatccactgt        1740
aaattgattg ttcagaatca aaacttccat tctcttcttt attattagaa cctattatcg     1800
aattagaaaa cttgattttg atttctaaaa aaatatttgg atttgtatag accaatccgc     1860
taaaaaaata atattttcca ccttcaacct cgaatctgtt gctccaagtt gaagagcctc     1920
cgattggagg ggttaaattt atataattga atttcctttg atttaaataa ttgtaatcaa     1980
ttataacttc gttacttcct ccaacattcc aaccaaaagc atcatcactc tcgaacgctc     2040
cattaataat taaattgcca tctgcaacac tctcaactct ttgtaagata ttatcactct     2100
ctatttgtat ttttgcgttt gttctttctt ctaaccctgt tatatctttc tcaactttac     2160
ctatcccagc tacaaattta tcagctaata attcgaattt accagttaaa ttaactatt    2220 tgctgttgta ttcttcggtg ctttctgaat acggtaataa caactctcct tcttgcagtg     2280
cgatttctct tacatcaagt aatatatcat ctaaaacaaa gccttgccct tctattccta    2340
tagccaatct agttttata ttgatttcac tcgtgaattt tgcaacacat aaatattcat     2400
tcgttccact atatgagttt ataatggtac tctcttctag ttttataacc tttattaatt     2460
caagcgtttc gttttttga tatttaattg ttatatcttt attttatgt gaaatacatt       2520 tgaattgtaa aatatattta gaaccttctt ttagttcaat aacatcgctt aaaattgcac     2580
aataaccact cgtttcttta gcagtcaacc ttatataatt ttgtgttaag ttattaaggg     2640 ttttacata ttccgttttc atcaaactca tataatttac ctcctatatc aatactttca     2700
ttttgtgctt tttctccatc agctttgaaa tacacccatt cctcaaaacc attctgtaaa    2760
gtagattttt tccaccaacg ttctttcatt ttgtattctt tggttgttcc tattatatca    2820
taacctttag aattagaatt tataacaaat gttccgttgt tacctgtatc aaacattttg    2880
attttatgcc attgtagtac tcctaaagcg tctgttctat gattgtgatt tatatctatt    2940
gttgttatta atgcagtttt tggcattgtt tcttcaataa attcaaaaga agtagagcca    3000
```

```
cctagaccgt gatgtccaac ttttaaaaca tcaactttcc ctatttctcc cttacaatct    3060
ttttcactag caatcgtcat atctccagct agtaaaaatt tgttttttgta atgagtgtaa    3120 acaactccta agcttctagt attgtaattg tcgtaaatct ctatagttgt atttataatc    3180
tgcaacttac tgtttttagt tatattataa agttctataa ctccaacttc tctactttt     3240 atattttat ttttaacaac ttctagcatt tttctatgtg ctgcacttgt tccccattca     3300
atttcttcta tgctatcaac tttattccaa tcagcctctc tataaaccaa ttcttttatc    3360
tcaaaattgt tagcaatctc ctcaaacgct cctatatggt cggtgtgtgc gtgagttgct    3420
ataaataaat caatactatc aacaccttgc tcttttaaat aattcacaac aatatcagaa    3480
gtttctttat aaccacaatc aaccattata tttttgttag cttcttgtat taatatcgca    3540
tcagcttgtc ttttagtatc tattatgtgt attttcaagt tagtttcatc attaaatagt    3600
gttaatgtcc cgttgtaagc actccaacca tccaaagaat taggcagtgt atttttttaat   3660 aaatttaaag cgtagttatt gtttaaagtt tctatagttt tacttacttc tcctcttatt    3720
tgtcctaaag aaacttcgaa ttctgttttta gttacaaagg tatcacctat agcgttttt    3780 atctcttcaa taacatcaat agaaagttta tcagtggtta tagttcccgc ttgtatatac    3840
tgtccactca tagccccgaa cgttattaaa ctagcattta tctttccgtc tatagtgaaa    3900
ccatattcat attttccata atagccagtt gtagaaaaac ctaagccatt tttattataa    3960
cgggtaacat taaccgcttt atttatatct ttattatcca ttataagtag ttcattcggt    4020
tttaaaacaa cataagaatc tttcaaccct gcgtttatca tgctatttat atagtcgctt    4080
aaatttgcat taggcttagt ttgtaattcc ttttctaatt ctgcgattat atcattaact    4140
gaaataggtc tactttcttt tttaacgtta gacaattctg tatttaatct tttttttcata   4200 gttacagaat aaactctctt aatacatcta gcttttattt tagttccata agtatcttct    4260
ataacttcga ctgtatcacc tatctcaaca gattcagttt gactataatc tttatattgt    4320
tctgttttag ataattctat gaaatttatg ttataagttg cttgtaattt atctatatta    4380
aataaagtaa attgagttct agctctttct tgtaaagcct gttgagcttg tgctaaagtg    4440 tcaaaaccttt catcgggatt attttcattt ttaacctttta tatctgaaaa ttccataact   4500
ttggtgtaaa cactactata attattaatt aattcacttt ctacaatagg agcttctatg    4560
ccatcaaaac ctctcggaac tatcctagtg caaaggtcat caacattcga tttaatttca    4620
aaccctgtta aattttttct tgatttaatc tgaacacctt tatcttgccc aaccctagta    4680
ttaattttgc agttgtattg ccttctgtag acctctccgc cccacctaac tataaaagca    4740
ttatctgcac cgaataaagc attatgaagg ctcatatttt gataataagc ggtactcgtg    4800
tcagatatat cagaagttaa gaaaaactcc ttgttacgtc ctgtagcatc attcaaaagc    4860
ttacttaaag ttgcttgacc attcatattt tccggtctgc aatctttaa gaacaacgtt     4920 aattggtcag ctattgtaat ttgccttgcg aatatagtga ttgttctttt atcttttctt    4980
atattgctta ttctaaagaa ctcatctccg tattcatcat ctagcgtgat gatagcttct    5040
tctattaagt tatcataaat gtattttaaa ctttcatctt ttttaactgc taggactatt    5100
tcagcataaa agtcatcttc tgtttgtgtt atagtcgcat ttataagaat ttcatctaaa    5160
aaagcaattc cgttagtaga aataacttct gctcttgtcg cagttcttga atgtaatttt    5220
gttcccataa ttccccctg tatctgtttc tagtattaat tttaagagta gtaaaaccgc     5280
taccgctaag agtgtttta cctctttta taataggtaa atctcctgtg cttgttatca      5340
```

```
cttgcatatt ttctttatta aaaatatttc tcatactatc tatgatcaca tctccagtat    5400
gtgtaaaact taaagtttca tcatttatgg tgatttgtgt ttctccctgt gtatttaatt    5460
ctataattgg taaagtatca atatcagaat cgcacatcaa aggagtgtta atatcccatt    5520
cttgaattat atcgtttgta tcaaaataga acggttcgca tagaaaagta atttcaaact    5580
ctatggcaac attcccattt ctactataat tgcctatgct tacctttta actttagagc    5640 aaatactatc attgttagaa agtatcaatc tattatcttc aatattagat aaccaattct    5700
ctattaatct tctttaacc tcccacctt ctctcttaac tctaactggt atagtgtgtt    5760
ttaaatcttt ataactccca gttttaacta taagagttcc gaatggattt ccttcaactt    5820
cttgttcttc ttctatttcc tcaactcttc ccatttctaa attattcatt gttaagagtt    5880
caaaatcatc ataacttgct ttattattaa aataaaattg tatcatttca tcacctcttt    5940
tatattataa catagaaaaa agcacccttt cgagtgctta aatttataaa tgttttatta    6000
tatcccaaac tgttatttgg ttcttatcct caaaatatct agtatcattt tgcatgctaa    6060
ttgctaacct cttgtagttt tcaacatctt catcagtaag tttagttaat ttatttaaat    6120
tttcatactt accaaataga gatttgatta tcttctgatg tactaaattc ttttaacat    6180 ctaaaactcc taactttct aagatagggt agaatagttc ttttgtaagt tgaagcttct    6240
ctctatgtgt taatagcata gaacctaatt taagatttgt ttccattgt ttgtagtata    6300 gttgttcaca ttcaaagaag tagtctctag cttcatgccc ttttttacat ttgcttatca    6360
tagctaaatg acttgctatt cttaaggata attcataatc tgtaaaagt tgattttctt    6420 ttatactccc tttgttattt gcaagtttaa ttttcacctc tttcacttct ctgaaagtga    6480
cctcaaagtc actttcgaca accatgcggg tttgagtggt attaggcaaa aactcaatga    6540
attttataaa gtcataactt gcagatagaa ggttttgact attccatcta tcgaatgttt    6600
tcttactccc taaccactta tgcaaatctc tagcactaac aaatttactc ccatcttctc    6660 ttactttat taattcttgt aataacatat tttattcctc ctttattcaa caaactttgg    6720
attcatataa aattctaatc cttgtggttg aaaaccttct ccaacttcta tataattcaa    6780
ttcatttaat aatttaacta tttttgctag tccttaatt tcttctccct ctttaattct    6840
tatccaatca aaagcgtggg tttcacctgt taaattttct cttaaaaacc aatcatctat    6900
ttctttcatt ctttcaaaat cttttctctt ttgttttgta ctttcatgat attttcatc    6960 gtactctatc gctattaacc ctatgagaaa atcaattcta tacttaccat tacataccga    7020
aacttgacta tcaaaagata aaccaaactc ttttaaaaaa cactttaaca tttcaccgaa    7080
ttcatattct ttccgatcag aattaaatac aacaacctct ttttctgttt cacctttat    7140 tttttcaga tactccaaag cttctttatt tcctaaaacc cctttggtat tctcaattac    7200
tttacttgct aaacttaatg ggatattgta ataaaaacga gtggaaaagc cattgttatt    7260
taatttataa ctttcattta ttttttctaa tcctaacttt tcaaattttc ttttgccca    7320 atcattatgt ctagttttta tttttaacat tttatgaaga tggtcgctcc taacaacaac    7380
ttcattttca caagtatttt ttgtaaattc tttcatacat ctcacctcct ttaattaaat    7440
tataacactc tttttgagta ttgtaaatag ttttgtgcgt aaaaaaagag aggaaaaccc    7500
tctcttatct aaacgctaaa gaagtcatac gagaatattc atcaaactca ctttgatgtg    7560
gtgctaaagt tctcatcatt tctttaccgt caatataaaa ttctactggt ctatttgcta    7620
agcttttaat ccagttttct aatttgtcta acggtataac cgcttccgct tgatttcctc    7680
tacctttgta actatctcct gcaacatatc ctcccataaa tgttggttgt gttactatac    7740
```

```
caccattgta taagtatggt actttaggaa gatttactcc gaagtgttta cctccaacga    7800
cagggacaaa gtctggtatt gttacactta ttttatttaa tccgcttata gcactattaa    7860
caagtcctat aactgcattt aaaggagctt ttattactgc acctaatccg ttcattattc    7920
ctccgaatat atttacaact ccttgccaag cccttgacca gttagcggta aatacacctt    7980
ttacaaattc tataatccca ttaaaaattt gttttacaga attaaatata tttttaacat    8040
tcgctagatg tgaatttaat atatctccta taaatccaaa agcattagac caatcaactg    8100
taaaagcgtt tttaatccaa tttataacag ttgaaaaagc ttctttaacc gcttcccaag    8160
ttccaacaac cacatttcta aatgtttcag aggtattcca tgcatataca aaagcacctg    8220
ctaaagcacc aagaagccct ataactatcc ctatcggatt cgccataaat accgcattta    8280
atattgccat agcaccacta aagctcttta ccatagttaa ggcagtaaat aaaggtttta    8340
caaatgcaat tataccactt acaatagcat agcccttat agccgctaaa taacctacta    8400
taacacttaa cgctaatcct atgttattta atattccatc taggtttccg ctttgtaaag    8460
cttgtacaag ccaactgata ccatctgtaa cgaatttaac cgcattagtt aacggttctg    8520
aaaacttttc gtacgctgct atacctaaac cttctagtgc tgatttaaaa ttgtccatag    8580
ccccttttaa gtttccactc atagttttag ccatttcctc agctgaacct tgtgagtttg    8640
ctatatgttt gcttaattca tcaaatctct ctccactatt ggcaagtaaa gcgttagcac    8700
tctttaaatc aactttgtta ataattcgc ttagaacttt agttctttct tgttctgtca    8760
tagttccgag tattttattt aaatcttaa atatttcatt tgtacccctc atattaccac    8820
ttgcgtcata aacttctaaa cctaattttt tcataagttt agcagctttg tctgttggag    8880
aacctaaaga aagtataatg tttcttaacg cagttcctcc ttccgcacct tttataccgt    8940
tgtcagctaa gattccaagt tgtgtattta attctactgt tccaccttta agagatttcg    9000
cagttccccc aactgttagt atagcttctc ctaattgtgc aacatttgta tttgcttct    9060
gtgaggtttt agccatttgg tcggtgaatc cttcaagttg gtctgtttct attcctaaag    9120
ctgacataga atccgtaact aagtcagaag cataggcaag gtcaattcct cccgccgctg    9180
ccaagttaag aactttaggt aatgcactta tagctttgtc tgtatcatat cctgcaagtg    9240
ccaagtagtt caacgcttca gctgattgtg aagcactata cttagttgta gctcccattt    9300
gtttggcggc atccgaaagt tttttgaagt tagaattaga agcatctcca actatacccca   9360
ttgttgcagc tacttgatcc atacttgctt caaaatccat accaactttc gttgctgcac    9420
ccgctgcaac tcctaaacct ccagctataa ctgcaccagc aacttagta gcttttccca    9480
ttctactcgc aacactttca gttttctttc cactttcatc tattttacta ttatagttct    9540
tattgtcaat gcttatttca gccattaaag tgaataaatt catctattca cctccttgs    9600
atttattata aatttctgtg caaatttctt caacattctt ctcttcttct tttacatttt    9660
gatttttcat attttcgtat aattcctcaa aactcttaaa cttttatct ctatttaaag    9720
attgagaaca tatccaaagc gattgagcca tatgccttt atgtgtccat tctaagttgt    9780
attcgttctc tttctctatt aaaactacat ttatagcctt aaaagaaagg gagcggaagt    9840
tactcaaata aataataact tttccactcc ctaaagtttt gaggattgct aaaaatttag    9900
aagttctta tcactccata attctttaa ttgtttgatt gttgtactg gatttgctt       9960
tctaatctct tcgaccgtct tatcatttac aattgctaat acattataaa tgttttcttt   10020
atgcttttta agaaggatag gaattaattt agtgaaatta ctcacacctt tagccaaccc   10080
```

-continued

```
tttgatttttt ccttctttct cgtccatatc agttatatct aatctatcat agaatataga   10140
gattaactct tcatcttgca taatttcgcc taaatacgga gttatttcaa ttacttttc     10200
tatacaaaca tcattattca tttcacttaa tttcatccat attctccttt atactaaata   10260
aatttctatt ggactttcgt ctggtttagc taaatcaata caaggggtta attctaaatc   10320
aaatttacct tttccttgat tttctatctc aaagtttaaa ccaccagtcg atattgcatt   10380
tttaactcta acaaccataa gtccatcact tttattaagc gttcccgccc aaactatttc   10440
tttgtagtcc ttagaaagaa aatggtttct tagagttatt ttcttccctg tacttcctaa   10500
agttgcttct tctgcgcaac ctatagccat taacattgtt cccgctttaa cttctgctat   10560
tttagtttta actttacagt caattttatt aaccgctaaa cagtccttat acatcccaac   10620
tgcaccgtca acatcttcca ttaaatctct tatgtctgga actatctcga tacttcctcc   10680
accacttgta gcacctaaca cattcgtcgg cgttcccata gcagttgtta ttgcatttct   10740
taaagcttct tcatccgaaa ctccttccca agttacacca gtcaaccaaa ctccagcatc   10800
taattgaaag ttctgtggtg tagtttgtgt caatccgttt aataatttca ttttatccct   10860
ccttataggt atattcttgc ttgtataacg ccatataaac gcttaatatt cggttcttca   10920
tcttgtaaca tttctccaaa cggagagcct ttatacaact gtatagagcc attagaagta   10980
aataccactt ttccattgct tatatcctcg cctagtaaat ccaatttact cgctacagtt   11040
tttaatgaag tcgatttatc ccatatagag aactgaatta aagcgtcgtc atagtttggc   11100
gtataactta aattgtaagt taggtaaggg aattgcgtac cttgcggaac gtttccctct   11160
aaaaatgaag gcatgatgct attaaaatag ctatacaacg cctttgaata ctctgtaaat   11220
ttttccacgt cgcaactcct ttccttattc taattctatc atatttatgc taaaacatac   11280
aactctgcac taagttgctt attttgaact ctagctcgtt taggtgtgat catatcctcc   11340
ggtctactcg taacccttag ataatcatta ccccttttaa caacatcgtt aaagttaaga   11400
ggcacattta tatcaactgt tatagtatat agcgatgtta ctccttgttg ttccgcaagt   11460
tttgcttgag tagagttatc taaacttata gcacccttaa aagttgctcc ctctatccat   11520
gaagtttcat atccacccat tccgtcagaa gctgttcttt tctccattat aatcagattt   11580
tctttataat catctagcat atttctttca cccctctttt atcccaaaat aattttggtt   11640
ttctatatgg ttttaattca tttgaaaaca cctcttgcca tgttaaagct tgaccttttg   11700
cattagttgc taagctataa gaataattcc caaaactttc acttacgata gcactcggtt   11760
tattttcact ctcatatgct tctatttttag ctttaaggct tattaaatcg cttggaatag   11820
caagagagga tattatcccc tcaaactctt catcttgcat cgtaaggctt tctagtgtta   11880
tattttgacc atctacaaaa gcgacccttat atacccatc atttagtgta ctgccttcta   11940
ttcttacata ttgacctatt atatatttac cttttactgt tatagtgtta gtgtttattg   12000
aatagcttcc tctttcgtaa aatttataaa agtaattatt tatagaattc aatatctttt   12060
ccatttatac acctctttttt attatttaaa aagcaataaa aaaagaact ttaatagacc   12120
tcttaatatt atctttatat ttctaatttg tagttcacaa taattatcaa tagtgaattg   12180
ttattctgat atcttaaacc attgcaccgt tatcggcgaa tttagattat taacccatgt   12240
agagtttacg ctatcccacc taatacatct aataacagca gtagtatttg tatcatttcc   12300
ctcgcttaaa tcttgtctta taattattat atcgtttttt atatttgtta aaggtggttg   12360
acttataaaa acttttcctt taacttttct attataagta atagtagcaa ttccattttc   12420
tgagatagtt acattcccac tatctaaata tttgtttcct actttaacag gaaatgagct   12480
```

```
atctttcaaa ttacctaaga aatcgtaaat atttccattg taatttattt ctggtcgcat  12540
tctgtttaca ttaaagttat aattaccgtt gacattgtca tattcgcaat tatctcgaat  12600
aataggcata ttgttattaa atatatattt atttgcatat gctgtcggaa atgaaggagc  12660
tgatattcca aaaccaccat ttatttttat agcatagttt ttacaaccac actcagtatt  12720
actaaatagt ctggtttctg catttcctgt tttgggcatt tgtttacagt tgtctaaagt  12780
taaactatat aaatcagaac caacaccaaa cataaaacta ttagcattgc attgtaatgc  12840
gaatatacaa tttataaatt tatagctttt cccatcaact tttataatac ttccacttttt 12900 ttcaatttga taatcgcact caaagttaca tccatcaaat acaacatatg aatttaaact  12960
taaatttatt gaatttatag atttcaaacc aaaattacaa tctctaaaat tagcttgtat  13020 tgatttaaa  atcaaaggtt tatcacattc attacagtac acttttttcaa atactacgcc  13080 gaagctattg ccgtcgctta tattagttaa aattccgttt gtacatctgt caattcttat  13140
tttgttaaaa aatacattcc atagaataaa tgtattagct attgataaat ctttattaat  13200
acctattgat attccatttt caaaattatc tattcttaga ttttcaaaat tcgaaaaatg  13260
cacctgataa ccttcttcat cattatttg tttaccaaac attaaaccac ttgtattatc   13320
ctttacacct gtgtttatta actgaaaatt actaatatta acatacctat catttacatt  13380
tataaaaaat gctgaacacc cttcgcataa tatttttgaa tatgaattag caatatctcc  13440
ttcgccataa atagttatat tttgtctatt tatatgaata ggttttttta ttttataatt  13500 acccttggg aaatataaaa cgctatttgt ttgcaataaa ttatttatta tatctgaatt  13560
atccgttaca ccatcgtttt ttacaccatg ttccaaaaca ttaacacaaa tatcatttat  13620
tttactcgta ttatgttcca attgtgaatc aaatttgtct aatcttctat ttaaattgac  13680
ttctccccct ctagcttgaa ctatctcact attagttgcg ctttcaaccc cattagtaat  13740
attagctacc gcttcatcaa attgcgtttg taatgaattg gcaatatttt gaaacttttt  13800
tacttcccct tggtactcaa cgacttcatt tttatattct tctgtttttt gattaaactc  13860
atttatttta ttttcatact taggaaattc caaattagcc ttttttgatgt attcttctat  13920 tttctttaac gcttcaattt catttgtgtt agcaataact tcaccactaa ccaatccttt  13980
tcctatctta aaagtagcat aagaacttgt tattcttcca ctagaatcag atatatctag  14040
ttgaaataat gcgtagcctt ctttattaaa tgcactattt ttaagtttaa cagtaacttc  14100
acctttgcta gcattcgttg gagttatttg gtcggtctgt tctaccaaag tcccatctat  14160
acgcctaaca taaaccttta tagtctgact ggataggtct ttaggcgtct tattttcagt  14220
tacaacaata tttaattcta cattatcttc ttgatttatc ccttcaattg gcactggatt  14280
tcttatcata gtatcaatag ttaaaggtat cttttttaaa gccatttctt cacttccttt  14340
ctatctaaat tatatcatat aaaagaaaaa gacgacaata ttttgtcgcc ctattctgca  14400
gtcatataac ctttagcttt taagtctttt agaagtttat tgaaccctgc taaaagagtt  14460
gccccatctt ctccgactaa ttcatctatt ttatcaagct taggaatcac cgcgtcagca  14520
cctttcgctc ccgctggccc tgctggcccc tgtagtcctg gttctcctct ttgtccttgt  14580
ggccctgctg gccctggtgt taattctata ttagcgattc cattctctat gttattcaat  14640
ttttctttag ttattaattc gtcatcagtc caagtgtgtt ttgaataagc catctttaa   14700 cctcctagac ttcttccttt ttagttctac ccttgccagt tttgccttc cctacttag    14760 aaagttcgaa ggcttcacta gggtgtagct acttttattt ttcttaatac acctgctttt  14820
```

```
cttgagttct ttaaaacaac tcccattact gcctcaactt caccatcaat tataaccca   14880
gtatcagtta catcttttg ataagtcttt attatcttat cacccgctgg tgaaatcccg   14940
tggaatcctc ctaaatctat tttaactcca tagatagaag tttctttaga agtatcgttt   15000
atatctatta tttctttagc tttagaaccg tcataataag tacctacaac ataaaaggt   15060
attccgtcgt agttgtctac tcctcttcca aaagcatctt ctgttcttgt gtaataacct   15120
aatttctag cgatagactt cattttaact gccattttgc tattcattat taagaaatcc   15180
ggtttctctt caaataaaga taaccactca tctaatgtat cagcaaacaa ttcagcattt   15240
tctgtcattt ttgcagaagt tgataagtca atagcctctg ccggttcgta ttctgtttct   15300
gtcccttcta aaagcttatc taatccatca aattcagggt tgcttccact tgcagtttta   15360
gctttatccc cttttattaa agcatagtta aataaattaa cagccccttt tatttttgt   15420
tgcatttgga aagcaacttc gtcgattgct ccacttgttt gagcgataac tctatcaacc   15480
ccgaagctac caccgaatat tttacaatca gcagtctttg cttctcttat tgcttcattt   15540
gcagtatagt tttctcctat cttctgaat tttgcagttg aaggagtttt taattgttga   15600
taaccatatg ttaatgtaga accaccagta cccggtgaaa ccgcattatc aaataccatt   15660
ttatctaaca atgttgattc tcttctaaac atatcaatta cagtttggtc gaccttatta   15720
gccataccga ctttactttg ttctaatgta agtgccattc gccttacctc ctattataaa   15780
tattttccta aagcatttgc tagaggatta tcattgtttt ctgtttgtgt atctcttggt   15840
ggttgtactg aacccaaacc actaacactc tcttgcttta taaaatcaga ataattttcc   15900
tttaacggat taactatgtt atcccaatct tttatagcat cattttcaat ctctaaagtt   15960
tctaaatcta tttctttagt taacaacttt agtattttt cgttgaatcc ttcttttttt   16020
agttgttcgg ttaataaacc tctcttctgt tcattaatct tttcaacttc tatgttattt   16080
ttatatgtgt caaattcact ctgtaaagct tcatatttac tcttatactc gtcagtattt   16140
gagttctcaa tcttagcttc taaatctgca atagtgttat taagttcatc tatagcacca   16200
actttcttat tgtattgttg cttagaaacg aactccttag ggatttctgc ttttatagtg   16260
tctgctatag tgtccactaa ctcaccttct aatccacatc tttttaatat tgcttttaaa   16320
tccatttata ttcctccttt acgtttttat agagttgtaa gctcttagga taatttaatt   16380
atatcaaata cgttataaat ttgtaaagtg cataaaaaaa agaacaccgt gaaagggtgc   16440
cctttttgca aaacacttta tcgtttggag gtactttat acttacatta tagcaaaaat   16500
agctttacgt gtcaagaatt ttcgtgagga ggaaacctcc ttcactctcc ccttgtaaca   16560
aaataaaaat ctaagttact acatttacta caaaaactac actaatttct atatagcaaa   16620
tatttataaa aaaatatata tataatttat tattataaat aaactcttga aaataaatgt   16680
agtaaatgta gtaaatatat ataaagctag tgataccaac ggtttgaagg ggttacaaaa   16740
atgtagtaaa agtgtagtaa aaaatgtagt aagcctaaaa atgtagtaaa acggttaata   16800
atatatgaat gaattttaac agtttatcaa taaggtttat tgttaaaaat gtagtaaact   16860
acaaaaatgt aaccgcaaaa tgtagtaaaa atgtagtatt actacataaa aatgtagtaa   16920
ctgaatccga aaatgtagta attgaaaata aaaaaaagac agtaaaatac tgccttaatt   16980
tattcccagt aatctcttat aaatggtatt ttgtaaccac ggattgattt accatcaact   17040
ttatatggtt ggttaggtat tcctctcctc ataagctcat tagcaagtgc tttcttttct   17100
tttatattaa gcttttcagc tatttctgta agcttgtaca ctctcaagtc gttacttttcc   17160
cagtctactt tatcatctaa tatgattgat atatctgttt gagcattaaa ttgtctatta   17220
```

```
attattttttt gtttcgcttc ttcctctttta gttaaccaat cgatactata attagtcaac   17280
cacatatcgt atactgcgcc ccaaaactca aacatattga aattgtcaaa ctcttctata   17340
ttacaagatt taacaggaat tacccaaaac cttcttgaac ctgtttcatc ttttaagaaa   17400
tcttttttgt taacattggc aatataactt gttagccttg gatatatttc agcgacacga   17460
ccaaacggaa ctctatattc atcggttgta ttagttaaaa actgcttaat tttaccttgg   17520
tcagctttta aagttgtatc taattctgct aactcaacaa gaatatattt agtattttgg   17580
atcacgctat cagttttatc ggggtctaaa gatactccat ctttgaataa gtcattaagt   17640
ggcattaatt tgcgtgcaaa cgttgattta cggcatcctt gttcaccttg gagtgttaat   17700
actccattag aactataacg gttttctaac tcattgtgag ccattttaac aacatttaga   17760 agccattat aaaacaaagt gaaataatac tctgcatctt ctaaagcatc atcttgaagc   17820
gttaaacact tttcaaacac atcaagcact atatcgtgat tatcatttct atacttcttc   17880
aacatatcta caaggggtt tatttctttt ctattagcta tatcaattaa atattcgtcg   17940
cataccgccc tattaagatt taaaccttct ttcacttgta aatcatatac aaatgtcagc   18000
atctcacctc ttttttttaaa cttctgcct tccatttgta aagttaattc atgagttatc   18060
ttattcataa ctggatttat tccataatga tttaacaaat attctaaatt tgccattgtc   18120
tttattggaa ctgttccgcc atcttttaaa tacttaacct ccggaaattg tataagagaa   18180
acgttgctct ttttattctt aacatcatta attgaaaaaa cttttttagt gttttgcatt   18240
ttaatatcct ccttatttac cattaactat ttccattata gcgatatgaa taggttttc   18300 acctctccaa ttatcaaacg ctttttttctc ttttcagta agatagaatt taacttgttt   18360
acttctctta cgattttca tattatcacc tcgcaagaca ataataacat agtgggtaca   18420
cacttgtaaa gtattttttt atttattgac aaaataatta agtaagtgta taattaactt   18480
ataaatattc ttaggaggtg ctattatgat tggttttttg ctaggcgttg acattacttt   18540
gttaattgaa atagttatac tagaaattat ttacgaaaga acgaataata aatggggcgt   18600
tttaagtaag atttcaacat atttaggttg gtgtatatac gcactaaatt taattatttt   18660 ttcgatttt gctataggaa gttttaaat tgtttattag gaggtattat catgggtaga   18720
tttatatgtg aagctattcc ttataatgga tttaaggaga gaattaaaat atgtaaggag   18780
ctacaaagaa aaagaatgag atttagtata gaaggaaata ttatatttgt ttattagagg   18840
agggttgacc ttctcttttt tttatgagat caaaacaaaa aaagaagag gattgctccc   18900 cttcttaaaa accaaaccaa ttaggtaaat tataaaacca gtcagctatt aaagcaccta   18960
taaaagctat agcaacaacc aatattggtg ctacaactgt aaaaaacata tttcttaaaa   19020
actttctata attccatttc ataattaaaa cctccaaact ttaattatac ttaaattata   19080
acatacttaa ttatattgtc aataataaaa taaaaaaaag agaggatttt ttcctctcgt   19140
cttaggggtg agtatatttt atcaaaggag aatttcatgt ccaactatat tatagcaaac   19200
ttaactatcg ttgtcaatct tttaacgttt gttcgattaa cttttttgtaa tcttccttat   19260 aatccattat agcgggtttg agtgttggtc ttgcgggttg cctactcgtt cccgcttcaa   19320
gaaatggagc gtattggaca ttagagccta tggcaacctt cttatcttgg gttttaactg   19380
cataattagc actattccta aatcttccag tatcaacaac tttcttagcg gtgataactt   19440
tttgccatat actaaccgct ttcaatccaa ctgcatttaa gcactttata accttgctat   19500
ccatttcttt tttgaataca ttggcgttgt tttcaaactt tattttcatt gctttaattc   19560
```

```
ctttaattttt ctttgcatac tttttatgtc tttcatcaag cttgttttgc ttcttttttgt   19620 ctttgacaat tcccttatta catcatctac tttcctgttg ccaaattgaa ttccgctgac   19680
tggatagtat tgtttcgcta aatctaaagc taccttgttt agttgctttt ctgtcataac   19740
ttttaattct ttatcttggt aaaatttaac tttattctta acttccttct tggttacttt   19800
ttttgctttt tctttagttg ttgttcgttt tttatttttcc tcttttgtta ttttagattc   19860
tttaatttta ttcttttctt cttttgaaac tattttctt tctttccttt cttgccactc   19920
ttcaaaactc attttcctaa gtgtttcatc aagttctttt tcttttctc cttttcaaa   19980 acctacaaat tcagtagtca tagtacatct acaacggatt acttcacttg ctccaccgtt   20040
aggatcaccc gggtacatta accattact aaaaggctta tccaagtcaa ctatttcacc   20100
attaactctc tgatgtgatt ccctagttct cttatccatt gtagctaacc aagatttctg   20160
aatctttaac cctttctttt ctgcaaattt ataactgtct aatctaccta cattttctat   20220
tctagtcgtt tcagttctag caattctaag agaatcatta tagttctttt cagttatttt   20280
tttaattctt gaagctatct gctgcatact ctcaccttgt agaagtccac taccaagagc   20340
tttctttaat tccttataca aagtagtctt atctgttaaa tcatcaatag ccatcaaggt   20400
aaacgggttt atctcttctt ttaataataa cttgatagcg tttctattat aaagtgtata   20460
ccctatatct ttagcaactg ccttttctac ttcataagca ctccaattat agtttaaaga   20520
gtaaatatct atcatatcat cgttcataat gtccatagca accttattag cattattaac   20580
aactagcgac atttctctta taatggcttc taaacgcttt ttctgttgta attgattata   20640
tatctgttgt ggttctttag cagtgtctat tcggcttata aggggtattta atttactttt   20700 taattctctt aaagcatcag aatataattc ttcaatattc ttttctagct tagcaaggat   20760
tttatcagtt tctttatgtg ctttatccat aatatcacct ctctttaatt atactaaaaa   20820
aagagatagc attacactac ctcttcataa gtcttttcga atatatcggg tttgcaagga   20880
taaaattcac ctttaatacc ttttataata taatcacctt ccgttgcggt tataactcct   20940
tctaaagtct ttatatcaca ataagatttt ccgtttatag ttttttctgt tctgaaattg   21000
taagcttttc catttgtaaa ttctttaatt tcttcaaaac aatctcgagt aaattttacc   21060
gcttctacta caactggttt ttttctatat ttcatgaaat cacctcctgt attaattata   21120
tcacaattat aaattaatta aaacctcctt cgggttcttt caatttaaat ttatcagcaa   21180
cttcttcatc tattagttgc ttttctaact taacatcatc tatcataggg tggcttctta   21240
aagcagtatc taaactcatt atagaagcac taacagaatt aattatatta ttaattactt   21300
ctgtttcatc tactaaccta tttctaacga aattaataga atatttctca ttaggttttt   21360
tgatgtattc taaatataat tggattatat tgtcacaaaa atctaagcaa ccagtttcga   21420
actcatctgt ctttaaatct aaatccatca tatttgcttt tatagcaacg ttggttaaac   21480
taccacccgc taatatagaa gtatcaagtc ccatggcatc agaataaata gatttattta   21540
gcatatttaa aatagtttct cttgcttgat atggcacttc tatagtgtga ggagttgcat   21600
cgccttcttc gtcaacattt atcattttat attgctttag atcacttaaa aagtcccccg   21660
cttctccgtt gtaattcttt aacgcccaat aaatatcttc gttatcttca aagttattag   21720
agaaatctga ataaacaatg tcgtataagt cgattttctg tttcaaagca aatgtaaatc   21780
tagatgtcct tatatcattt gcatataaag ggaatatcgg aagtctactg aatccttctt   21840
gtccgatttc tctctcctct atagcatctt taacggtctt gataatgtaa ttcttcttag   21900
attctgttat ttctatcttg ttcttatcac acttatactc tgtctttcca tcttcttcat   21960
```

```
acagttctat ccacataggc ttatcagtat ctatttgcca aaatcttatc cccgctctaa    22020
cttgacctgt cctttcatct tctaacggta taaattcagt tcctctccat atatcaatat    22080
caaattgtcc tttagagtta ataaaacaat aaccccaacc cacaccgtct acaagcgcag    22140
cagttccaca tcttttaagt ttaatatcga atttcttccc taaaccttct ttgacttttt    22200
cttctgtcat aagcccgttt gctaatagat aactaacctc ttgcttaatt atcttaggaa    22260
atagcgtatt agcgatttta ttattagcct taaacttatc tactacttgc cttcctaaac    22320
tatcataaag ccatttaaga cggttttta tctttgtatt ttcttctcta taatatgctt     22380
gtgcttctac agcattatta tatttactcg ttccttaaa ttcttgtata gcctggagga     22440
taaatgaagc tttatcccca ctagcttgaa agtcttggaa tgttttcatt ttattcctcc    22500
ttttctagtt ctctctttaa ataaaatata gccttctcta atcttgctt tttattccct     22560 ttgtgttcgc atctagcaat gtatttaata gcgttaccta agaaaaacc aagttcccag     22620 tcctctataa catctataac ctcataacca cctttattat aatggcttgg atggtttacc    22680
atatcagctt caacatcttg tactttaaca gctatatgct tagcgttttt ctcccaataa    22740
ccatatccac aatagaatct ttctccgttt tctaaaactt cataatgaac aaagtagtct    22800
aaaaaatcta aagccttaac tctttcacct tctaagtcat atatttcatc ttttttatat    22860
ttcatcttaa tacctcctaa aaaatcttat ttgcactaaa gctacgtttc tgttttcttc    22920
ttgctatatc cattatagca tacctaaccg cgtctatata gtggtcgttt ccatcgggat    22980
atttacttat aaactgccca tctttattca tctcatactc ataccctata aattccttag    23040
cggcgtttgg ggttcttttc ttatcaatta caatttcatc taacatctgc aaaaatttat    23100
aagtgaaatc cctactatca ggtccttttt tagcttttg catattcaag ccataccctc     23160
tcatttcaga gatggattta ggatcagcac tatctgcaac aataggcttc ttatagatat    23220
ttggttcttt ttccagtatt ttatcagtta gcttttatt gctcaatccc tgttcgtata    23280
tttcatctat aatataaagc ttgttgttct tataatggat tttacaccaa gttgcagggt    23340
ctatactaaa tccaaagtca acaccatact caaattcctc catattattt atttcctctt    23400
ttgttatttc tcttataatt acattatcaa atacatttcc accagttcca gttacttcac    23460
ctaaatattc atgtttgtaa gcttcttctt ttacattctt tagatgttca gcttctatta    23520
tgaattgttg ccctaaccaa tcagacggaa cagttaaata ggtactatgg tggatcaacc    23580
tgtcttctct atcaattagc tgctcttcat taacccagtt attcttagat ttaggagggt    23640
taaaagtata aaacacccag ttatcaccat tctttcttat aaaagactgt gtcatacttc    23700
ttatctcttc catgccattg aactggtcta actcctcata ccacacaatt cctattctac    23760
cgaatggaac ggttataccct ttagctttca tagggtcgtc gcaacctaaa aagacaattt    23820
cttgattagt tggagtataa acaatcttca aaggagattt ataaaccttta aaataaccat    23880 ttaatcctaa atcatttata gaccaaatca tctgattata aacagaacct tttaatgtct    23940
gccctacttt tctgactata acagcgtggc aatcattatt agccattata agaagaggaa    24000
taaccttaga tacaaacgaa ctcttggtac ttcctctccc tcctttaagc atataatggg    24060
tgtgattatg ttccataaca tcataaagta aatcatcgaa gttcggtgct attttctcca    24120
aaaaattaat ctctcttgaa tacaatgtta acaccttcta cctttttgatc tacctctttc    24180 ttatctgtcc aatcatagtt atttttttaat gcaaatataa tccctgttgt cggttgtcct    24240
gaactttgca atctttcttc tgtattcatt agcactcttt ctttagccct ttttacagtg    24300
```

```
ccgaaatacg cttcttttt  accatagttt  ataagggttt  gcctgtctat  ttctaagtaa   24360
tacgctaaac cgctcatagt catagggttt  tcattgattt  cacaatactc  aaaatattcg   24420
tctattcttc ttttaactc  ttcttctgtt  ttgaataaca  aaggtcttcc  catacctcta   24480 caccctcgctt tctatctata ttataccata tttacacaat aaaaatacac ctctttcgag    24540
gtgtgaatta ttagtcattt ataccatt   ttccttttat  ttcttctgtt  gaaaatattt   24600
taaccgcctt atattcatat attgttttat aatcttttct ttttatttt  attgcatctt    24660 cataaatttc gtatttaaaa ccactctcac aactttctat ctctttccct tcctcgaaag    24720
cttcaaacgc ttcttggaat gtgtattgtg atcttttaag tttgaacttt ttctcttttt    24780
ttatacctat ttcacgacaa ttaaaataat ttgttttatg ttttaaaacc aactcacttg    24840
ttttattatc aagataaatt tcaagcattt cactctccca aacttctcct tctttatat    24900 tagcaattac ctctctaaaa gttaattctt tcatattaac actcacttct tttcgatta    24960 tttcaaacat ttcttctgtc cacatccaac cgtcttcatc tatatctata tcataagata    25020
aacaatcata caccctctaca attgttgcta tcctaccttt aagtgtttcc atatagccac    25080
cgcaaaacat ttgttctcca taataactac caacaattaa atcttctcta accttcactt    25140
tatctccaac ttttaacatt ttaccactc  ttaacatctt tctcttttcaa taattctttc    25200 ttaccttta  gcaaagtttc tttatgtcct tttctctcat ttatagcata ttgttgtttg    25260
atagcactag ctaagtccat tatctcccct cccacaactt aatactttcg attctctcta    25320
taggaactat tatttcccct tgttcgtctt ccattttac  tctataatca tgtatctcta    25380
atattcttcc ttttatctct gacattccag tatttaagat tacaaaatct ccatcttgga    25440 aataaaccc  gttttctcct actaaataat taatgctcac ttttctaatt gacatttatt    25500
tctcctccca aaacttttct atctcatatt gatttatttt tctcgctttt tctctctcga    25560
ttctttcaag ttgccttgct atcttagctt cttttataaa ctctaaatga tttaattctg    25620
aatctgtcat gaacaatttt aactgctcta gcataaatttc aacatctgca atttcttcaa    25680
cgaagttctc ttgaaaatgc aagtcgtttc taacacactt agaaattgca agtattagtt    25740
ctgctaactc ttcttgtgtt tgccttaatt gtggttcttt gccataatag ttggcaattt    25800
gaattaattt tgattctcta ttcatgttca acccccaaaa tttatttaca acttaattat    25860
aacatactta attattttgt cgatagttat ttattcatct tctaaaatta tttttgcaac    25920
cttataccct tgcctgtttt taacatcttt atcaattaaa ttctttgttg agctatccca    25980
acaacctaaa aacgctgatg tttcttttat agtatcaaac agttgtataa taggctcacc    26040 cttttacattg caatcataca ctgcataaca aacctctctt tgcgttctag gtcttttctg    26100
tttttcctct ttaaattcta taaatttcaa attgcttctt ttgtttcttt tattactctt    26160
tatttgtctt gatatcatat tatggtttat attcattaat ctacccaaag ctctttgcga    26220
atccgctatc gctataggta atccaaatac atctttattg aatgctaata ccatcttaaa    26280
ccctcctaat ccactcttct ggaatactta aattatattc ttgcgctaat ataaacgcca    26340
ctttagaaaa attagtaatt ccatagactt tttagcgac  tgatattaaa ttaccagttc    26400
cgcaatgtgt aaagcaagtg taaataccttt tttcatcatt tataactaaa gcccctttat    26460
tatctccacc atgcaaaaca catctaccaa tataattgcc attcacacgc ttaaattctc    26520
cacctagatg cttctgtatg aagtctttta agcttataga cgatattagt ctatttaaac    26580
actcttcttt atattgtggc ttaatataat cctcaccgtc atacttggta tatccttgtt    26640
caataacttt ttgcttagct ttgttatccc tctttaactt agattgataa gcatttataa    26700
```

```
gttttaccat taatgcgcaa cttataggaa tgtcgttctc tctgtaagtt acttctttat    26760
ttgtcccagc ccatatacga tttgcgttac ttgtagcttg atctaaatat ttattaaatt    26820
tccattgtag agccttatac aacaacttat aagtttctac atcaatagga ctttctaatc    26880
tataaatcaa tctgaattta gtgtaatcag tatcactaaa agttggatat tctattatag    26940
gataaacacc tagtttctta ttaactagtg caaccatttc aaataatgtg atctcatttt    27000
ctttactatc tacatctaaa gcaatacact ccaaacaatt aatgctgctt tcaaatatat    27060
ctttactacc ttcttgaaat tcagctaata aaacagaatg acctcttttt aaatattctt    27120
ttatttctct ataatcaacg tatatacaag ggtaattttt catacccatt gtaatatcta    27180
tcatatcagt tgcagttggt ttaacttttat aacctttctg acttacttta atcttaatca    27240
tctacctaac ctccaaaacg aatttacaag ttaattatat aactacttaa ttatcttgtc    27300
aacactttta ttaaaaagac tagattttac tctagtctat aaactttatt tattttctcc    27360
caagtatttc tcctaactct tttgtctctt atttctacac ctaaataagt gtgatatggt    27420
attcctataa gtttagcagc ttcttcaata gttaatccta actctttacg tttagctttt    27480
atcttttctc tatttataaa aacatctttc atagtctttc ttgattttttc tctagctttt    27540 tcctttaaac attctttaca catagaccta taaccatctt ttccttgtgg gtggtgatag    27600
aaattagttt ctatatcttc gaatgctctg ttgcaattag tacaaatttt catttattca    27660
cctaaaatgg acattcttct tttatttctt caagaaaaga attttctaat ccattccctt    27720
tattttcttg tttgttatta ccacttataa aatcaaaagt ttctacaact acgtcagtag    27780
tatatctttt agtcccgtct tgagcttcat aacttccagt tcttatattt ccgcttatag    27840
caatttgaga acctttagag aaatattgat ttattatatc ggcagttttta ccgaacgcta    27900 tacaatttat aaaatcagct tcatctttct tgaactttct gtttactgct aacgtaaatc    27960
tagcaatatt agtattaccct gttctataat ctacatcttt gcttaaacgt cctaataagt    28020
taacctgatt catattatta cctccttagt tggaaaagtg aggcgtacaa gatataggcg    28080
aatattttat tctcaacact ataaactcac tcaaccaact taaatttatt tacaatttaa    28140
ttatatactt attgatttat tttgtcaaga catttactac ataaaccttg ttcacacaat    28200
aaaactttgt aatctacaaa tggaatatga ggttttaata aatctatcat aataaaagcc    28260
aattctctaa tctctttctg tgcatgaata cactttcttt gtcttaaaaa gtttctaaag    28320
ttatttaaat ccattgtaac tattaaatta caagttgttg cttgtggtaa tattgctcta    28380
gcatcttctt ttttaattcc taattctatt aaatatctat acatttcttt ggaatgttca    28440
aaaaattctt ttaaatcttc ctttgctatt ttaccctttg tttcattcat ataatttaaa    28500
ttaggcataa caaaatcaaa gttactacca tcaacatatc tttgcgactg aacattaaac    28560
ttaaatgttc tatgtctagt caactgtgct aaacacgctc tcgaaattcc ttctatagca    28620
aaactaaaac taacgtgctc aagaggactt aaatgccctt ctaacataag cggcatcacg    28680
aaatcacaca tttctttatc gctttttaatt tttatatcat tccacccttt tgcactataa    28740
catattcggt aggatttaaa aatcttttct atgggattag gagttatatc tatcaattca    28800
actttcattc tatattacct ctctttcata aatccatttta taacctttttg attgcttgta    28860 tttgttttga caacacctaa caacgcttgc tctatctata tttaatttct tcttaacctc    28920
taaagcgctt gaaaaattac atataaatcc acttttttaaa ttaattccta taactggttt    28980
tcgataattc ttttgtttgt cattgtaatt attgttgtaa acagcgtcgc accattctaa    29040
```

```
attacaaagt ctgttgtcat cttttatctc atttatatga ttaacttgtt ctttattttt    29100
aggcatatca acaaaactca ataaaaccac tctgtgaacc ctcgcttgtt tttttattcc    29160
atttttacac agagtaaaat acaaatatcc atccttatcc tttgtagttt taattatttt    29220
tcctttaact tttctaccta aagaatctat tctatctagt gattttattc ttcctaaatc    29280
acttgcctga tataaacctt cataattagg tatatctctc catttctctt taatcacttt    29340
ctattctcct ttaactcttt aattataatc gcagtagcaa ccccaccaac tgtaacacct    29400
attaaaatag gtttagctaa gatactgcta ttaggatagg ctattaatcc cattaaagct    29460
attcctacac ttgtaattaa acacgcttta ctatcactca ttcaattcaa cccccacatt    29520
aaaatttctt aaaagataat ttctaacttc ataatataaa gtgttgtata tctcgctccc    29580
catatattca cttggtattg cttctatagt agtgttgtat tcagcttcaa agccttttat    29640
cctagcgtgt aatgttttag gttcgtacct acttctatac ttcccttctc ttaaatgctt    29700
atgaaataat ttatcctcta taaacaatct aaccttagta ttattagctt ttaaaatagc    29760
aaactcttta cttattcttg gataatcaga actactaaaa ttacttgcta tttcatctat    29820
agaagctttt ctttcaacta ctataagctt atcaaaatat aaatcccttt ctatgccttt    29880
cagagcacct ttgggaagga aacaactata atcaccttgt tctaatttct gaaccttaaa    29940 agttttttc ttagccttaa accacgctaa tacgtggtcg ttggcttttt ctcttgtatc    30000
aactattata gttaagtctt ttaatgcttt ttttatttct gtttcagtaa atctatatct    30060
cattattttt gaactttctc caatctacta caaatgttat cgtactgatc tttagtcatt    30120
tgacttatat cagatactcc aaattctttt acgcattgag cagttatagt tgcttggttt    30180
attcctttag attttcctat agcaaacaat ctgcttaatt gcttatctga taaaccttcc    30240
tttggcttag aacttccatg agtagttaaa tttgcatcat catcttcgcc tgtattaaga    30300
tttaaaatag cttgatatga ataccttcta agataagtta ttaagctacc tgcttgttgt    30360
gggtcgtttt taactggttt catgaataac ggttcactct ctatatattc cccactctca    30420
tgtagtaaaa tagtctgtat tcctattctt ccagtttctt tgcttaacgg catttgtaag    30480
actgacaaac cattcttctg caatatatcc ctagttgcta atataagctt atcaagtgtt    30540
acataatcac ttttgaagaa tggatttta gcatcttttg atatacttgt tacttcggca    30600
ttgaacttcg ctaaagcaac tgctaattta actattgttt cacttctatt cataaaaata    30660
cctcctttta actgacaatt taattataca ccaacttaac taccttgtca atcatcttat    30720
ttttaaactt tcctcttgca ctaatttagc cccttctatt ttctcgccat ttttcaacgc    30780
ttctttaagc attttcttat ccacgctagg agtatttaca ataaattgtc tcggtatagc    30840
gtttaaatcc tctacaatcg ctttaggagg gttttctttt acacttacag taaatatacc    30900 accttgact tctctcttct ctaatccgtt tatagtatca aataaatacc cttgtaagtt    30960
ctcaatctta ttctctctta tctttcgttc tcttgctaat cttttttctt ccgcttttaa    31020
cgcttccgct tctgcttgta ggttttaat taatctcacg atattttcta cctttgtaga    31080
taaatcgcac tctaatcctt tcatagagtt tataactaac tcttttaaat tttcatcttc    31140
tcccgcattt tctaaaactt gttgtaagtt tctaagtttt tgtgataatt catatagttt    31200
cattaaataa ctccctcctc tttaaactgt tttatataag gtcttaaaac cttaactgct    31260
tctgattctt taggacaacc aattataaaa gcgattcttt taataaatct agttgttaac    31320
tccggacttt tataagccgc catgttggtt ttgcaagtcc tttcttccat tcttctccaa    31380
tcttgaagag cttttctgat ttcactttc ttaataacca tcataatacc tcctcgatgt    31440
```

```
tctctacaag tataattata gcgtacttaa ttatcttgtc aatacttttt tctaaaaaat    31500
aattatgggg tgatgaggtg aaaatatttt atttcattat tcgtctcgga gcatctttga    31560
accattataa gaaataaaaa ttaatcactt actacatttta ctacaaaaac tacatcattt   31620
tctatatagc acatttttat ataaaatata tatattattt tattacttat aataaagtct    31680
tataattcaa tgtagtaaat gtagtaaata tatataaagc gttggtatca ctagcttaca    31740
aagggtttta aaaatgtagt aattatgtag taaaaaatgt agtaagctta aaaatgtagt    31800
aaatatttta attaattatg aattgattgg taacattttg tttataatta agtgtagtaa    31860
atgtagtaaa actacaaaaa tgtaacttaa aaatgtagta aatgtagtaa taaaaaaaga    31920
cacctattaa gtgcctttat aatggtttat ttatattgtt gtttgtagag catcatagta    31980
taattcttta aataccctagc atactcataa gcttcctttg tagtcttgca agtctttgtt   32040
tgtaataatt cgttagcgat tttatcaata ttcttcataa aaaatacctc ctaaagcttt    32100
atattttata tatatgctct aagaggtaaa aagattactc ttttttcttca atttctttaa   32160 ctttatcatg aagcatttta tcaaccaact tgatataact tgcatcatat ccagtaaact    32220
caaagtcttg taaccatctg cgtatctttt ctatttcttt agaaactccg caaaggggtt    32280
ttaagacttt ttcagattct ttagggaatt tagcgactaa tctattagat atagaagcta    32340
tagtggtata aacttcgatt tcccaatcta aatacaattc taaatgttcc tttatagata    32400
aaggttcttt aactccttct aattcctccc aagacggttc gaggttttcg ctgaacatat    32460
caattacata gtgttgtaaa tccaccctat gacatctatc ctctttagat tgaactttat    32520
gccatctttt aaaccctttgt aaccctttca tgtgtgctga cctgctaagg gtatcgtgaa   32580
tcatttcacc tctagcgctt aaatttatag cttcttttaa tagttttata gcttcattgt    32640
taaaatcata actcttaatc atgttttata tccctcaatt tcatcatagt gttgttatac    32700 attttttgagt gaagtatttt catatcttcc attaattcat ttataacagt cattattgct   32760
tttgtaccgg cttctaaacc atgtttattt attatcttgg aaatacactc cataaactct    32820
gtatcttctc ctaatggctc gtaaaccatt ttagctgatg aatattccat ggttttatct    32880
ttttctagca tagattctat ttttaaagca tcttttatat tatcaagcgc catggtcata    32940
gcttcaacac attcacaatc ccatttatcg gttaccatag ctttctctat tttaggcaaa    33000
gctttatcaa ttatctttcc gttaacttct attatttat tgtaatccat catttacccct    33060 cctttagcaa tcttataatt tcattatttt gctctataat ggtatttaat tttaagttag    33120
tttcttgctt taattcttcc ataagttcat cattagaagt ttgttttaga ttctcggtgt    33180
agtttaatac acctaagaat ccactaaaca aagctaaagc gtctaaatct cttaattgat    33240
tattcacttt cagaaactcc tgtagccaca taagaagtag gacaaactgg actttctact    33300
aagaaatgag aagtatcatt tccataaact actttgtact ttctcctact tctaatttgg    33360
tctgctctta aaatattacc ttttctacat aaaaccggta tagttgcagt tccgttcaaa    33420
attacaactg gcaacgttcc agcattgcta ggaattgatt gacaagttat taaacaatat    33480
tctttcaaat ttgttaatgt tgttgttgga atagttatgg ttaaactttg gtttggtaca    33540
gttccggtga ctgctatact tgtacttttt attattctat tacaatattg acaactcata    33600
agtcgtcctc ctttatttaa aataaaaaga gaggtatgtt atacccctct ataaaatcaa    33660
cctctatatg aggaatctta attagcaaag attataattt tctccgcaac catacggtgt    33720
gaatggaaca cattgaacag ggtaaggtct tacttgactt actatatttg cagtttgtgc    33780
```

-continued

```
cgcttgactt aatccaagtt ccgctgcttg aagtctatct ctcaaatctt gtatagtatt    33840
ttgagttaat aaggctcttg tagcttcacc atcagcgtgg atagcgttag ttatagcaca    33900
agtgttcttt tcagcctcat atctgttgat aagtagttct ttttgcgtat tacaacagca    33960
actagctatt tctgaactca aatctttaaa ttgtgctaag ttattatatc ctaagctaca    34020
taaaccttgt tgaagagtat tcatattata agtgttttgg tcgcttaatc ttcctagttg    34080
gttagaaagg ttagaataaa ggaagtcatt gttaatagtg ttaaatcctg ctccattacc    34140
tccaaatcct ccgaaaccat ttcctcccca tgctaaaagg aaaaataaga agaaaattaa    34200
gcttccgcca cctccaaaaa atccatcgtc attttttattg tctaaattgt atactggtgt    34260
tactcccagt ccttctgtca ttgccatttg caatcactcc tttactatta ttattttatt    34320
agtgccttcg cccacaacta cagcaccttt tcgtcttata actttaccgt aaacgctttg    34380
ataatttaaa tttaattctt cacaaacaga agataattgt cttttttttac cgtttaccaa    34440 aacaaatttg ttgttacttt tattccttga ttgttctttt aaagatatcc acctacaatt    34500
agatggagaa taatcttttt gacaatcaat tctatctaaa gttaaatcat ctttataacc    34560 atttttttaaa gaccaatcaa taaaattcat tttgtctgaa acccattctt tacaaacttt    34620
aatacctttt ccaccccaat ttttaaaatt aagagtatta ggattgtaac atcttgtcat    34680
cattgaataa tactctttgt acaatctttc gttagacaat ccatgttttt tggcttttct    34740
tgattgaatt tccttacgta agcaaccaca agatttcgtg ctttttaaaat tattagatgc    34800 cactaaagtt tcattgccac aatcacatct acacaaaaac aacttgtgtc catctttagc    34860
tttaccactc tcttttaaga ttgttaacct tcctattttt tctccatttt tcttcataaa    34920
atcactcctt atgttaatat gcaattatta taacataaaa agcatccgat ttcaattaaa    34980
acttaatacc aaattgttga gccatctgtc tgacttgttc ctcgctcatt cctttttgtt    35040
tagcaatatt cataatagtt tcttgaattt gttgaggatt tttgccttct aacatttttct    35100 ttgcttgtcc catcatagga ttattaccaa acatattcat tagttgcata ggatttatat    35160
ttcccccttg catcatttgc attaattgca tcggattaaa attattcatt tttattacct    35220
cctaattggt ttaataaact atctaataca ttcttataat tgtctaaatc gcttttttaag    35280 gcgttatatt cttctttagt acaataacct tctgtcggtt tttcttcctc tatagaaagc    35340
gtataagtat ctatatgtgg caaaccgttc atatctatat atttagtgta taatttcttg    35400
tttgttgtat cttcaaacca caatttgctc ccatcgaagt tcggagttat tcctctaact    35460
tcttctatag atgtaactgg tcttatagaa ggaaattgag gttgttgaac ttgttgtatt    35520
ggttgtggtt gttgttgttg attaaaactgt tgttctaaag cgttcaatct attattcgca    35580
aagttaggat tgaaattagg attcattcca taatttccat atcctccata taaggattc    35640 atattattac ctcctgttct ttatacttta attttacatt aggttataat ggttcttaaa    35700
tagaaataaa tagtaagttt taggtaaatt aaacgtaaaa aaagcaccct ttcggatgct    35760
ttaatattat tcttccatat tccttatatt aaaaattacta taactatta aaattgattt    35820 tatacacatc atagataatt gtaagttata atttataaat cttactcttt gtatactctc    35880
tctgtctgtc ttaggttgtc cgtgtttatt tagatatta cttacaaatg ttttacaaa    35940 atccattgga acatctatag cacctatttt tagactatct aaatcccagt taacttttac    36000
ccaagcaccg gttatctgtc tatcaaagaa tcttaaagct tgattttctt gagataataa    36060
ttgatttctt tcttttgatta tctgtaattc ttttctaac ttttctatat ctgcattttt    36120
agttagataa taaccatctt ttcttatctg cttaagaatt ttcttaactt ccttcttaaa    36180
```

```
ttgttttgct ataggttttc tgctttgcat taatacttca tacaatccat cttctgttaa    36240
aaatgtcatt tctcttgatt gaatcatatc tggtgtcttt attgtagata ccagcttttc    36300
ttcttcatct acaaccgaaa ccatttggct tactttatat ttcccgtttg attttgaata    36360
atctatccat tcagctacat ctttagctaa aaataatggg ttttctatat ctccataaat    36420
tttaaattcc tttgataata cctcttgttg tttaaaaact tttaattctt tcattttatc    36480
cacctatctt tcttatatta aatttagatt ttattattaa cctatataaa tcaccttccg    36540
ggattaatgt cattgtttgc gtatttctcg cttcattatg tgcgttccca ttttgggaag    36600
ccacattaac tacttctttt attccatctc tccttctttt ctgttattct ctcttaattc    36660
atataacccc tccaatatat ctaaaggtgt aatatatca tgattaactt ctatataaga    36720
aattatcata tctagttgtt cgtctgtcat ttatctcacc tcctgtaatt ataataacat    36780
ctataaaggt tataaaaatg acaaaaatat tacaatttgt aatttgaata aaaaaagagt    36840
agatttctct actcttaatt gtttaatatt tctctttta atttatttaa tttcatccca    36900
taataactta caatgggtat atttacaatt cctattataa tagcaaacgg ggaaaataag    36960
gttaaaaata aacttaatat aataattaaa gcagatatag aaaaacaatt gcctattctt    37020
ttatacttag catctaaatc attattccct tttatctttt cctctataac tccaagctct    37080
gcaactcttt gttgtgcttt attttgcttt aatatttttt cttgttgttt tcttttcttt    37140
ctatttcttc taaaatcatt tatttcacca gctacccaaa ttttggttat gaactctaac    37200
atttaaaaca ccttcctaaa ccctaaaaat ctcattctc tttcaatctc ttctttagtt    37260
ccctcaaatg taacctcttt aatatcatta ttccaaatat aatataaaag attttcactt    37320
gctatcttta acgcttgtaa tggttgttct ccctcttcaa ctaaatcatg atacaattca    37380
aaatcagcat gattatttcg gttgagagtg taagaaacac cctcacattc atataaagcg    37440
ccaacctcaa aataattatt cataatatcc ctccaaatca aattcaacct gataatctct    37500
ttctgttatt ttttatctt taagattttc ataatcttt ctagttcctt ttacaaatga    37560
aaaggcggta tgtgcatcta tatcatatat tattgctaaa agtaaagcat aataaccgtc    37620
attcatattt attcctccaa ccaactatta aaagtaccac aatagttatc ttcgtacatt    37680
cttaaatcat cttcaagttc ttcaattctg tctatagcag tatctaaagc atcttcaaaa    37740
tttcttcttt catctataag ttctcttatt ataaaaaccg cttttctct gtcttttaaa    37800 tcttcaatag agcatatacg ttctccagtt tcactatcat ataaaaactt tccattaaat    37860
tctatgttca tcttcttcaa tctcctcatt cattattatt tctgatatag cttttttctat    37920 accacttata acaccggcat aaaagaaatt tttattttca aaaccttctg atctttcttt    37980
gtattgttct tttaagcttt ttaacgcttt taaagtgttt cttttcatat taataacctcc   38040 taaacatctt atgatttaat tataacatag ttaattatct tgtcaatagt tttatataaa   38100
aaagagagat atctctaccc ctctaaaatc ttcttaatta attcttgatt ttcccaagct    38160
ttagataatt tcttataagc tttatttcta taattggtaa cacttttaat actacaatct   38220 attttttatag aagctttctc ttgtgtcata ccccttatat ccactaattc aatcgctaaa   38280 cgttcttat cttaaggtt aaccaattct aaggctaaca ttagaagagg tttagaaggg    38340
caatcaagca ccttctttat atcttctcta ttcataagat tacctctttt tcttaaatct    38400
tacttttctt tttcttgtta ctgttttctt ttgcctaact cccatttaac ctactccttt    38460
aatttatcat tatggattga attatcatta tagttattac catttattat ttgactttcg    38520
```

-continued

```
ccatcagaac tttgttcata agttgtagtt gtttcctcta ccaattcagc ttcataatta  38580
gcaaagaagt aaatagtact accacacatt attgttatac ttaaaaccac tgtagctaaa  38640
caagctaaac aaatcttttt ataaccttct aacgtttgtc tttggtgttt cattatttcc  38700
ataaaggttt catttgataa taattgaatt tccttatctt tgtccataaa tacctcctat  38760
ttgttaagtg ttacacttgc tataaacgca attatagaac ttattatacc agcaactatt  38820
aaatcccaac gcttactggg tgttgatttc aaatcgatta tatctctttt catttccgtt  38880
aaagtttcca ttatagtttt atattgatat tcttgaacgg agtgattctt ttccatctct  38940
gcaattcttt tttcgtgttc cctaacttct tttcttaatt gcataagttc actatattgg  39000
ttatcattac attccattta ttttccacct ttcggcaagt cgattcctcc agtttcggga  39060
ttattcatta atccgagtag cactgctata ctacaaacta atttaactgt tgtatctgcc  39120
cattctgcat ctattacata tccaaattga tttaataaaa gaacaattaa acctacaaga  39180
gaaatccaaa gggcaggatt tttgaaccta gcccaatatt ctttattttt tatactatta  39240
aacatttaga tcacctctat atctttttcag taaagcaata ataacctaac tcatcgctta  39300
ttctttgttg tgctttttca gcatcttctt tatttgtaaa tctttgtacg caaactctat  39360
aatagtcctg ttccttttct agtggtatat tagggtcgat agcatttgct aaatatctag  39420
ccataacctc gtatgggatt ggtgaccaaa tggaaa                           39456
```